(12) United States Patent
Kimble et al.

(10) Patent No.: US 6,730,820 B2
(45) Date of Patent: May 4, 2004

(54) AGENT AND METHOD FOR MODULATION OF CELL MIGRATION

(75) Inventors: Judith E. Kimble, Madison, WI (US); Robert H. Blelloch, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/321,987

(22) Filed: May 28, 1999

(65) Prior Publication Data

US 2002/0102210 A1 Aug. 1, 2002

Related U.S. Application Data

(60) Provisional application No. 60/129,023, filed on Apr. 13, 1999, and provisional application No. 60/087,170, filed on May 29, 1998.

(51) Int. Cl.[7] .......................... G01N 33/00; A01K 67/00
(52) U.S. Cl. .................. 800/3; 800/13; 800/8
(58) Field of Search .................. 800/3, 8, 13; 435/375; 424/9.1

(56) References Cited

FOREIGN PATENT DOCUMENTS

| EP | 0 874 050 A2 | 10/1998 |
| WO | WO 87/04925 | 8/1987 |
| WO | WO 97/29635 | 8/1997 |
| WO | WO 98/55643 | 12/1998 |
| WO | WO9961656 | * 12/1999 |

OTHER PUBLICATIONS

Blelloch R et al. Dev. Biol. 216:382–93, 1999 (abstract).*
Colige A et al. Proc. Natl. Acad. Sci. USA 94:2374–2379, 1997.*
Kuno K et al. The J of Biological Chemistry 274:18821–18826, 1999.*
Rudinger J in Peptide Hormones. Editor Parsons JA. pp. 1–7, 1976, University Park Press, Baltimore.*
Blelloch, et al. "Control of organ shape by a secreted metalloprotease in the nematode *Caenorhabditis elegans*," Letters to Nature 399:586–590 (Jun. 10, 1999).
Abstract: Braz. J. Med. Biol. Res. XP–002118307.
Blelloch, et al. "Control of organ shape by a secreted metalloprotease in the nematode *Caenorhabditis elegans*," Letters to Nature 399:586–590 (Jun. 10, 1999).
Abstract: Braz. J. Med. Biol. Res. 32(7)805–812, 1999.

* cited by examiner

Primary Examiner—Ram R. Shukla
(74) Attorney, Agent, or Firm—Quarles & Brady LLP

(57) ABSTRACT

A GON-1 migration protein in *C. elegans* and a gon-1 gene encoding same are disclosed. The protein, termed GON-1, shows structural similarity to a protein produced by an up-regulated RNA in an advanced tumor cell. Although the tumor cell protein has not previously been identified as having any role in cell migration, it is disclosed herein that the related GON-1 protein is required for cell migration and is involved in shaping tissues or organs. It is deduced that the protein is also a target for modulators of cell migration and tissue shaping.

9 Claims, 3 Drawing Sheets

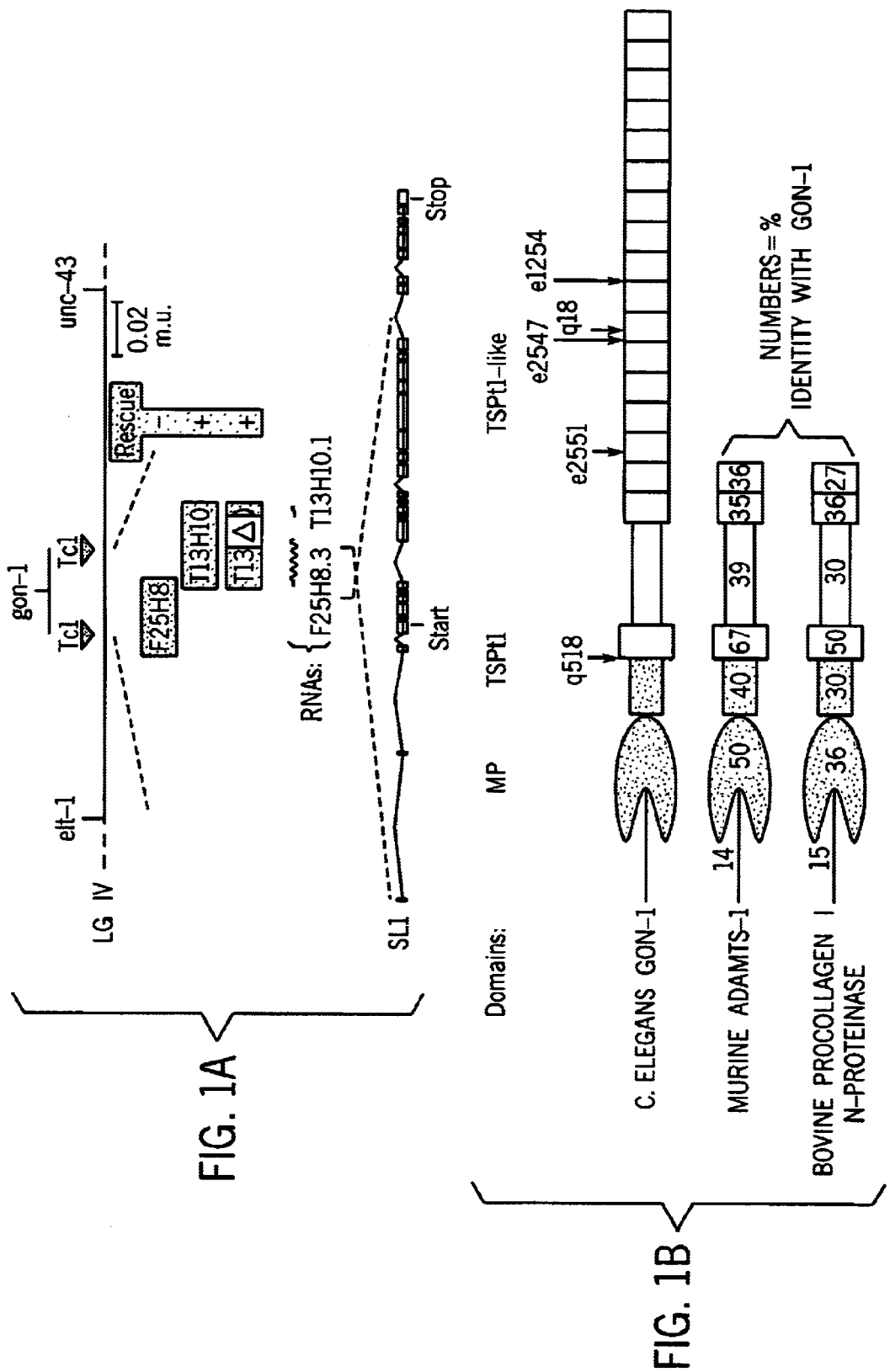

FIG. 1C

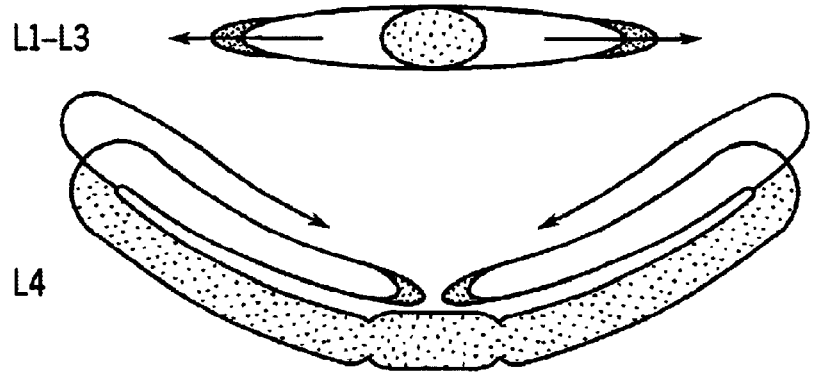
FIG. 2A — A. WILD-TYPE GONADOGENESIS
L1-L3
L4
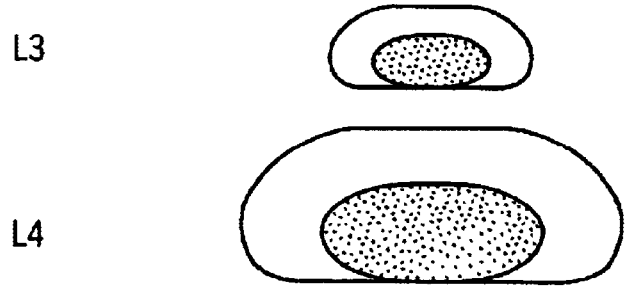
FIG. 2B — B. gon-1 REQUIRED FOR GONAD MORPHOGENESIS
L3
L4
KEY: ▦ SOMATIC GONAD   ☐ GERM LINE   ⟩ DTC

SEQUENCE LISTING

<160> NUMBER OF SEQ ID NOS: 5

<210> SEQ ID NO 1
<211> LENGTH: 6659
<212> TYPE: DNA
<213> ORGANISM: Caenorhabditis elegans
<220> FEATURE:
<221> NAME/KEY: CDS
<222> LOCATION: (1)..(6450)

<400> SEQUENCE: 1

```
atg cgc tcc atc ggc ggc tca ttc cat ctg ctg cag ccc gtc gtc gcc      48
Met Arg Ser Ile Gly Gly Ser Phe His Leu Leu Gln Pro Val Val Ala
 1               5                  10                  15 gct ctc ata ctc ctc gtc gtc tgc ctc gtt tat gcg ttg caa tca ggg      96
Ala Leu Ile Leu Leu Val Val Cys Leu Val Tyr Ala Leu Gln Ser Gly
            20                  25                  30 agt ggc acg atc tca gaa ttc tca tca gat gtg ctg ttc tcc agg gcc     144
Ser Gly Thr Ile Ser Glu Phe Ser Ser Asp Val Leu Phe Ser Arg Ala
        35                  40                  45 aag tac tca ggt gtg cca gtg cat cac agt cga tgg cgt caa gac gcc     192
Lys Tyr Ser Gly Val Pro Val His His Ser Arg Trp Arg Gln Asp Ala
    50                  55                  60 ggt ata cac gtc atc gac agc cat cac atc gtc cga aga gat tct tat     240
Gly Ile His Val Ile Asp Ser His His Ile Val Arg Arg Asp Ser Tyr
65                  70                  75                  80 gga cgt cgt gga aaa cgt gat gtc acg tca aca gat cgg cga cgt cga     288
Gly Arg Arg Gly Lys Arg Asp Val Thr Ser Thr Asp Arg Arg Arg Arg
                85                  90                  95 ctc caa gga gtt gcc aga gac tgt gga cat gct tgt cac tta cga tta     336
Leu Gln Gly Val Ala Arg Asp Cys Gly His Ala Cys His Leu Arg Leu
            100                 105                 110 cga tca gat gat gcc gtc tac atc gtt cat ttg cac aga tgg aat caa     384
Arg Ser Asp Asp Ala Val Tyr Ile Val His Leu His Arg Trp Asn Gln
        115                 120                 125
```

```
ata ccg gac tca cat aac aaa agt gtt ccc cac ttt tcc aat tca aat      432
Ile Pro Asp Ser His Asn Lys Ser Val Pro His Phe Ser Asn Ser Asn
        130                 135                 140 ttc gcg ccg atg gtc tta tat ttg gac tcg gag gag gag gtt aga ggt      480
Phe Ala Pro Met Val Leu Tyr Leu Asp Ser Glu Glu Glu Val Arg Gly
145                 150                 155                 160 gga atg tct cga aca gat ccc gat tgt atc tac cgt gca cac gtt aaa      528
Gly Met Ser Arg Thr Asp Pro Asp Cys Ile Tyr Arg Ala His Val Lys
                165                 170                 175 ggt gta cat cag cac agc atc gtc aat tta tgc gac tcg gaa gac gga      576
Gly Val His Gln His Ser Ile Val Asn Leu Cys Asp Ser Glu Asp Gly
            180                 185                 190 ttg tac gga atg ctt gca cta ccc agc gga atc cat acg gtt gag cca      624
Leu Tyr Gly Met Leu Ala Leu Pro Ser Gly Ile His Thr Val Glu Pro
        195                 200                 205 att att agt gga aac gga aca gag cac gac gga gca agt cgc cat agg      672
Ile Ile Ser Gly Asn Gly Thr Glu His Asp Gly Ala Ser Arg His Arg
    210                 215                 220 caa cat ctc gtc cga aag ttc gat cca atg cac ttc aaa tcg ttt gac      720
Gln His Leu Val Arg Lys Phe Asp Pro Met His Phe Lys Ser Phe Asp
225                 230                 235                 240 cat ctt aac tcg acc agt gtc aac gag acg gag acg acg gtt gcc acg      768
His Leu Asn Ser Thr Ser Val Asn Glu Thr Glu Thr Thr Val Ala Thr
                245                 250                 255 tgg caa gat cag tgg gaa gat gtt att gaa cgc aaa gca aga tcc cga      816
Trp Gln Asp Gln Trp Glu Asp Val Ile Glu Arg Lys Ala Arg Ser Arg
            260                 265                 270 aga gct gcc aac tct tgg gat cac tat gtt gaa gtc ctt gtg gtg gcg      864
Arg Ala Ala Asn Ser Trp Asp His Tyr Val Glu Val Leu Val Val Ala
        275                 280                 285 gat aca aaa atg tac gaa tat cac gga aga tct ctt gaa gac tac gtt      912
Asp Thr Lys Met Tyr Glu Tyr His Gly Arg Ser Leu Glu Asp Tyr Val
    290                 295                 300 ctc act ctc ttc tcc aca gtt gcc tcc atc tat cgt cac caa tcc ctt      960
Leu Thr Leu Phe Ser Thr Val Ala Ser Ile Tyr Arg His Gln Ser Leu
305                 310                 315                 320 cgt gca tct atc aat gtc gtt gtt gtc aag ttg atc gtt ttg aaa acg     1008
Arg Ala Ser Ile Asn Val Val Val Val Lys Leu Ile Val Leu Lys Thr
                325                 330                 335 gaa aac gct gga cca cga atc act cag aac gct caa caa aca ctt caa     1056
Glu Asn Ala Gly Pro Arg Ile Thr Gln Asn Ala Gln Gln Thr Leu Gln
            340                 345                 350 gat ttc tgt aga tgg cag cag tat tac aat gat cca gat gat tcg agt     1104
Asp Phe Cys Arg Trp Gln Gln Tyr Tyr Asn Asp Pro Asp Asp Ser Ser
        355                 360                 365 gtc caa cat cat gac gtt gca atc ctt ttg acg cgt aaa gat att tgt     1152
Val Gln His His Asp Val Ala Ile Leu Leu Thr Arg Lys Asp Ile Cys
    370                 375                 380 cga tca caa gga aaa tgc gat aca ctt gga ctt gct gaa ctt gga aca     1200
Arg Ser Gln Gly Lys Cys Asp Thr Leu Gly Leu Ala Glu Leu Gly Thr
385                 390                 395                 400 atg tgt gat atg caa aaa agt tgt gca atc ata gaa gac aat gga ttg     1248
Met Cys Asp Met Gln Lys Ser Cys Ala Ile Ile Glu Asp Asn Gly Leu
                405                 410                 415 agt gct gca ttc aca att gct cat gaa ttg ggt cat gtg ttt tcg att     1296
Ser Ala Ala Phe Thr Ile Ala His Glu Leu Gly His Val Phe Ser Ile
            420                 425                 430 cct cat gat gac gaa cga aaa tgc tct acc tac atg ccg gtt aat aag     1344
Pro His Asp Asp Glu Arg Lys Cys Ser Thr Tyr Met Pro Val Asn Lys
        435                 440                 445
```

```
                                                     -continued aac aac ttc cac ata atg gca cca acg ttg gaa tat aac act cat cca    1392
Asn Asn Phe His Ile Met Ala Pro Thr Leu Glu Tyr Asn Thr His Pro
        450                 455                 460 tgg agt tgg tcg cca tgt tca gct gga atg ctc gaa cga ttc ctc gaa    1440
Trp Ser Trp Ser Pro Cys Ser Ala Gly Met Leu Glu Arg Phe Leu Glu
465                 470                 475                 480 aat aat cga ggt caa act caa tgt cta ttc gat cag ccg gtc gaa cgt    1488
Asn Asn Arg Gly Gln Thr Gln Cys Leu Phe Asp Gln Pro Val Glu Arg
                    485                 490                 495 cgt tac tac gag gat gtc ttt gta cgt gat gaa cca gga aag aaa tac    1536
Arg Tyr Tyr Glu Asp Val Phe Val Arg Asp Glu Pro Gly Lys Lys Tyr
                500                 505                 510 gat gct cat caa cag tgc aag ttt gta ttt gga cca gct tct gag ttg    1584
Asp Ala His Gln Gln Cys Lys Phe Val Phe Gly Pro Ala Ser Glu Leu
            515                 520                 525 tgc cct tat atg ccg aca tgc cgc cgt ctt tgg tgt gca aca ttc tac    1632
Cys Pro Tyr Met Pro Thr Cys Arg Arg Leu Trp Cys Ala Thr Phe Tyr
        530                 535                 540 gga agc cag atg ggc tgt cga act cag cat atg cca tgg gcc gac gga    1680
Gly Ser Gln Met Gly Cys Arg Thr Gln His Met Pro Trp Ala Asp Gly
545                 550                 555                 560 act cct tgt gac gaa tca aga agc atg ttc tgt cat cat gga gcc tgt    1728
Thr Pro Cys Asp Glu Ser Arg Ser Met Phe Cys His His Gly Ala Cys
                565                 570                 575 gtt cgt cta gcc ccc gaa tcc ctt acc aaa att gac gga caa tgg ggt    1776
Val Arg Leu Ala Pro Glu Ser Leu Thr Lys Ile Asp Gly Gln Trp Gly
                    580                 585                 590 gac tgg cga tca tgg gga gaa tgc agt cgt act tgt ggt ggt ggt gtt    1824
Asp Trp Arg Ser Trp Gly Glu Cys Ser Arg Thr Cys Gly Gly Gly Val
                595                 600                 605 caa aaa gga tta aga gat tgt gac agc cca aaa cct cga aat ggt gga    1872
Gln Lys Gly Leu Arg Asp Cys Asp Ser Pro Lys Pro Arg Asn Gly Gly
            610                 615                 620 aag tac tgt gtt ggt caa cga gaa cgt tat cgg tca tgt aat aca caa    1920
Lys Tyr Cys Val Gly Gln Arg Glu Arg Tyr Arg Ser Cys Asn Thr Gln
625                 630                 635                 640 gaa tgc cca tgg gat act caa cca tac cgt gaa gtt caa tgt tct gaa    1968
Glu Cys Pro Trp Asp Thr Gln Pro Tyr Arg Glu Val Gln Cys Ser Glu
                645                 650                 655 ttc aac aat aaa gat att gga atc caa ggt gtc gct tca acg aat act    2016
Phe Asn Asn Lys Asp Ile Gly Ile Gln Gly Val Ala Ser Thr Asn Thr
                    660                 665                 670 cac tgg gtt cca aaa tat gcg aat gtt gca cca aat gaa cgt tgc aag    2064
His Trp Val Pro Lys Tyr Ala Asn Val Ala Pro Asn Glu Arg Cys Lys
                675                 680                 685 ctg tat tgt cgg ctc agt gga tct gca gcg ttc tat ctg ctt cga gat    2112
Leu Tyr Cys Arg Leu Ser Gly Ser Ala Ala Phe Tyr Leu Leu Arg Asp
            690                 695                 700 aaa gtt gtt gat gga aca cca tgt gat aga aat gga gac gat att tgt    2160
Lys Val Val Asp Gly Thr Pro Cys Asp Arg Asn Gly Asp Asp Ile Cys
705                 710                 715                 720 gta gct gga gct tgt atg cca gca ggc tgt gat cat caa ctt cat tca    2208
Val Ala Gly Ala Cys Met Pro Ala Gly Cys Asp His Gln Leu His Ser
                725                 730                 735 act ctc cga aga gac aaa tgt ggt gtt tgc ggt ggg gat gat tct tcc    2256
Thr Leu Arg Arg Asp Lys Cys Gly Val Cys Gly Gly Asp Asp Ser Ser
                    740                 745                 750 tgt aag gtt gtc aaa gga aca ttt aat gag caa gga acc ttt ggt tat    2304
Cys Lys Val Val Lys Gly Thr Phe Asn Glu Gln Gly Thr Phe Gly Tyr
```

```
                755                 760                 765
aac gaa gta atg aag att cca gct ggt tct gca aat att gat atc cgg        2352
Asn Glu Val Met Lys Ile Pro Ala Gly Ser Ala Asn Ile Asp Ile Arg
    770                 775                 780 cag aaa gga tat aat aat atg aaa gaa gat gac aat tat ctt tct ctc        2400
Gln Lys Gly Tyr Asn Asn Met Lys Glu Asp Asp Asn Tyr Leu Ser Leu
785                 790                 795                 800 cgt gcc gcc aat ggt gaa ttc cta ctt aac ggt cat ttc caa gta tca        2448
Arg Ala Ala Asn Gly Glu Phe Leu Leu Asn Gly His Phe Gln Val Ser
                805                 810                 815 ctg gct cgc caa caa att gca ttc caa gac act gtt ctc gaa tat tct        2496
Leu Ala Arg Gln Gln Ile Ala Phe Gln Asp Thr Val Leu Glu Tyr Ser
            820                 825                 830 ggt tct gat gca att att gaa cgg ata aat gga act ggt ccg att aga        2544
Gly Ser Asp Ala Ile Ile Glu Arg Ile Asn Gly Thr Gly Pro Ile Arg
        835                 840                 845 agt gac att tat gtt cat gtt ctt tct gtt ggt agt cat cca ccc gac        2592
Ser Asp Ile Tyr Val His Val Leu Ser Val Gly Ser His Pro Pro Asp
    850                 855                 860 atc tca tat gag tac atg act gcg gct gtt cca aat gct gta att cgg        2640
Ile Ser Tyr Glu Tyr Met Thr Ala Ala Val Pro Asn Ala Val Ile Arg
865                 870                 875                 880 cca ata tcc agt gca ttg tat ttg tgg aga gtt acg gat act tgg aca        2688
Pro Ile Ser Ser Ala Leu Tyr Leu Trp Arg Val Thr Asp Thr Trp Thr
                885                 890                 895 gaa tgt gat aga gcc tgt cgt gga cag caa tcg caa aaa tta atg tgt        2736
Glu Cys Asp Arg Ala Cys Arg Gly Gln Gln Ser Gln Lys Leu Met Cys
            900                 905                 910 ctg gac atg tcg act cat cgt caa agt cat gat aga aat tgt caa aat        2784
Leu Asp Met Ser Thr His Arg Gln Ser His Asp Arg Asn Cys Gln Asn
        915                 920                 925 gtt ctc aaa cca aaa caa gca aca cga atg tgc aat ata gat tgt tct        2832
Val Leu Lys Pro Lys Gln Ala Thr Arg Met Cys Asn Ile Asp Cys Ser
    930                 935                 940 aca aga tgg atc act gaa gat gtg tct agt tgt agt gcc aaa tgt gga        2880
Thr Arg Trp Ile Thr Glu Asp Val Ser Ser Cys Ser Ala Lys Cys Gly
945                 950                 955                 960 tct gga cag aaa cgt caa cga gtt tct tgc gta aaa atg gag ggt gat        2928
Ser Gly Gln Lys Arg Gln Arg Val Ser Cys Val Lys Met Glu Gly Asp
                965                 970                 975 cgt caa act cca gca tcc gaa cat cta tgt gat cgt aat tca aaa cca        2976
Arg Gln Thr Pro Ala Ser Glu His Leu Cys Asp Arg Asn Ser Lys Pro
            980                 985                 990 tcc gat att gcc agt tgt tac att gac tgc tct gga aga aaa tgg aac        3024
Ser Asp Ile Ala Ser Cys Tyr Ile Asp Cys Ser Gly Arg Lys Trp Asn
        995                 1000                1005 tat gga gaa tgg act tca tgt tct gaa act tgc gga tcg aat gga aaa        3072
Tyr Gly Glu Trp Thr Ser Cys Ser Glu Thr Cys Gly Ser Asn Gly Lys
    1010                1015                1020 atg cat cgg aag tca tat tgc gtt gat gat tcg aat cgt cga gtt gat        3120
Met His Arg Lys Ser Tyr Cys Val Asp Asp Ser Asn Arg Arg Val Asp
1025                1030                1035                1040 gag tca ttg tgc ggc aga gaa cag aaa gag gcg aca gaa cgg gaa tgt        3168
Glu Ser Leu Cys Gly Arg Glu Gln Lys Glu Ala Thr Glu Arg Glu Cys
                1045                1050                1055 aac aga att cca tgt cca aga tgg gtt tat ggg cat tgg tca gag tgc        3216
Asn Arg Ile Pro Cys Pro Arg Trp Val Tyr Gly His Trp Ser Glu Cys
            1060                1065                1070 tct cga agt tgt gat ggt gga gtc aaa atg cgt cat gct caa tgt ttg        3264
```

```
                                                       -continued

Ser Arg Ser Cys Asp Gly Gly Val Lys Met Arg His Ala Gln Cys Leu
    1075                1080                1085 gat gca gcc gat cgg gaa aca cat aca tcc aga tgt ggt cca gca cag      3312
Asp Ala Ala Asp Arg Glu Thr His Thr Ser Arg Cys Gly Pro Ala Gln
1090                1095                1100 aca caa gaa cat tgt aat gaa cat gct tgt act tgg tgg cag ttc gga      3360
Thr Gln Glu His Cys Asn Glu His Ala Cys Thr Trp Trp Gln Phe Gly
1105                1110                1115                1120 gtc tgg tct gac tgc tca gct aag tgt gga gat ggt gta cag tat cga      3408
Val Trp Ser Asp Cys Ser Ala Lys Cys Gly Asp Gly Val Gln Tyr Arg
                1125                1130                1135 gac gct aat tgt acc gat cgt cat aga tca gta cta ccg gaa cat cgt      3456
Asp Ala Asn Cys Thr Asp Arg His Arg Ser Val Leu Pro Glu His Arg
    1140                1145                1150 tgc ctt aaa atg gaa aag ata att aca aaa cca tgt cat aga gaa tca      3504
Cys Leu Lys Met Glu Lys Ile Ile Thr Lys Pro Cys His Arg Glu Ser
1155                1160                1165 tgt cca aaa tat aaa ctt gga gaa tgg tct cag tgt agt gtt tct tgt      3552
Cys Pro Lys Tyr Lys Leu Gly Glu Trp Ser Gln Cys Ser Val Ser Cys
1170                1175                1180 gag gat gga tgg tcg tca aga aga gtt tca tgt gtt tct gga aat gga      3600
Glu Asp Gly Trp Ser Ser Arg Arg Val Ser Cys Val Ser Gly Asn Gly
1185                1190                1195                1200 act gaa gtc gat atg tca ctt tgt ggt act gca tct gat cgg cct gct      3648
Thr Glu Val Asp Met Ser Leu Cys Gly Thr Ala Ser Asp Arg Pro Ala
                1205                1210                1215 tct cat cag aca tgt aat tta ggc act tgc cca ttt tgg aga aat act      3696
Ser His Gln Thr Cys Asn Leu Gly Thr Cys Pro Phe Trp Arg Asn Thr
        1220                1225                1230 gat tgg agt gct tgt tct gta tct tgt gga atc ggt cat cgg gaa cgt      3744
Asp Trp Ser Ala Cys Ser Val Ser Cys Gly Ile Gly His Arg Glu Arg
    1235                1240                1245 aca acc gaa tgc ata tac cgc gaa caa tct gtt gat gct tct ttt tgt      3792
Thr Thr Glu Cys Ile Tyr Arg Glu Gln Ser Val Asp Ala Ser Phe Cys
    1250                1255                1260 gga gat acc aaa atg cca gaa act agt caa act tgc cat ctt ctg cca      3840
Gly Asp Thr Lys Met Pro Glu Thr Ser Gln Thr Cys His Leu Leu Pro
1265                1270                1275                1280 tgt aca tct tgg aaa cca agt cat tgg tcc cct tgc tca gtc act tgt      3888
Cys Thr Ser Trp Lys Pro Ser His Trp Ser Pro Cys Ser Val Thr Cys
                1285                1290                1295 gga tca gga att cag act aga agt gtt tcg tgt act cgt gga tct gaa      3936
Gly Ser Gly Ile Gln Thr Arg Ser Val Ser Cys Thr Arg Gly Ser Glu
        1300                1305                1310 gga act att gtt gat gaa tat ttt tgt gat cga aat act cgt cca cgc      3984
Gly Thr Ile Val Asp Glu Tyr Phe Cys Asp Arg Asn Thr Arg Pro Arg
    1315                1320                1325 cta aaa aag act tgt gaa aaa gat act tgt gat ggg ccc aga gta ctt      4032
Leu Lys Lys Thr Cys Glu Lys Asp Thr Cys Asp Gly Pro Arg Val Leu
    1330                1335                1340 caa aaa ctt caa gcc gac gta cca cca atc cga tgg gca acc gga cca      4080
Gln Lys Leu Gln Ala Asp Val Pro Pro Ile Arg Trp Ala Thr Gly Pro
1345                1350                1355                1360 tgg aca gcc tgt tca gca act tgt ggt aat ggt act caa cgt cgt ctt      4128
Trp Thr Ala Cys Ser Ala Thr Cys Gly Asn Gly Thr Gln Arg Arg Leu
                1365                1370                1375 ctc aag tgc cga gat cat gtt cgt gat ctt cct gat gag tat tgc aat      4176
Leu Lys Cys Arg Asp His Val Arg Asp Leu Pro Asp Glu Tyr Cys Asn
        1380                1385                1390
```

```
cat ttg gat aag gaa gta tca aca aga aat tgt cgc ctt cgt gat tgt      4224
His Leu Asp Lys Glu Val Ser Thr Arg Asn Cys Arg Leu Arg Asp Cys
        1395                1400                1405 tca tac tgg aaa atg gcg gaa tgg gaa gag tgt cca gct act tgt gga      4272
Ser Tyr Trp Lys Met Ala Glu Trp Glu Glu Cys Pro Ala Thr Cys Gly
    1410                1415                1420 act cat gtt caa caa agt aga aat gtt aca tgc gtc agt gcg gaa gac      4320
Thr His Val Gln Gln Ser Arg Asn Val Thr Cys Val Ser Ala Glu Asp
1425                1430                1435                1440 ggt ggt cgg acg att ttg aaa gat gtt gat tgt gat gtg caa aag aga      4368
Gly Gly Arg Thr Ile Leu Lys Asp Val Asp Cys Asp Val Gln Lys Arg
            1445                1450                1455 cca aca agt gca aga aat tgc cga ctt gaa ccc tgt cca aag gga gaa      4416
Pro Thr Ser Ala Arg Asn Cys Arg Leu Glu Pro Cys Pro Lys Gly Glu
        1460                1465                1470 gaa cat att gga tcc tgg att att gga gat tgg tca aaa tgc tct gct      4464
Glu His Ile Gly Ser Trp Ile Ile Gly Asp Trp Ser Lys Cys Ser Ala
    1475                1480                1485 tct tgt ggt ggg gga tgg cgt cgt cgc agt gta tct tgc act tcg tct      4512
Ser Cys Gly Gly Gly Trp Arg Arg Arg Ser Val Ser Cys Thr Ser Ser
    1490                1495                1500 tct tgc gat gaa acc aga aaa cca aag atg ttt gat aaa tgc aat gaa      4560
Ser Cys Asp Glu Thr Arg Lys Pro Lys Met Phe Asp Lys Cys Asn Glu
1505                1510                1515                1520 gaa cta tgt cca cca ctc aca aat aat tct tgg cag ata tct cca tgg      4608
Glu Leu Cys Pro Pro Leu Thr Asn Asn Ser Trp Gln Ile Ser Pro Trp
            1525                1530                1535 act cac tgt tct gta tcg tgt ggc ggg gga gtt caa cgc cgc aaa atc      4656
Thr His Cys Ser Val Ser Cys Gly Gly Gly Val Gln Arg Arg Lys Ile
        1540                1545                1550 tgg tgt gaa gac gtg ctt tcc ggt cgt aaa caa gac gat atc gag tgc      4704
Trp Cys Glu Asp Val Leu Ser Gly Arg Lys Gln Asp Asp Ile Glu Cys
    1555                1560                1565 tca gag att aag cct cgc gaa caa aga gat tgt gaa atg cct cca tgc      4752
Ser Glu Ile Lys Pro Arg Glu Gln Arg Asp Cys Glu Met Pro Pro Cys
    1570                1575                1580 cga tct cat tat cac aac aaa aca tca tca gca tca atg aca tca tta      4800
Arg Ser His Tyr His Asn Lys Thr Ser Ser Ala Ser Met Thr Ser Leu
1585                1590                1595                1600 tca tct tcg aat tca aat acg acg tct tcc gct tcc gct tct tcg ctt      4848
Ser Ser Ser Asn Ser Asn Thr Thr Ser Ser Ala Ser Ala Ser Ser Leu
            1605                1610                1615 cct atc ctt cca ccc gtc gtc tcc tgg caa acg tct gca tgg agc gcg      4896
Pro Ile Leu Pro Pro Val Val Ser Trp Gln Thr Ser Ala Trp Ser Ala
        1620                1625                1630 tgt tct gca aaa tgc ggt cgt gga acg aaa cga aga gtt gtc gaa tgt      4944
Cys Ser Ala Lys Cys Gly Arg Gly Thr Lys Arg Arg Val Val Glu Cys
    1635                1640                1645 gta aat cca tca tta aat gtg aca gtg gca agt aca gaa tgt gat caa      4992
Val Asn Pro Ser Leu Asn Val Thr Val Ala Ser Thr Glu Cys Asp Gln
    1650                1655                1660 acg aag aaa cca gtt gaa gaa gtt cgt tgt cgt act aaa cat tgc ccg      5040
Thr Lys Lys Pro Val Glu Glu Val Arg Cys Arg Thr Lys His Cys Pro
1665                1670                1675                1680 aga tgg aag act act act tgg agt tcg tgt tct gtc acc tgt ggc aga      5088
Arg Trp Lys Thr Thr Thr Trp Ser Ser Cys Ser Val Thr Cys Gly Arg
            1685                1690                1695 gga atc aga cgt cgt gaa gtt caa tgt tat cgt ggt cgc aag aat ttg      5136
Gly Ile Arg Arg Arg Glu Val Gln Cys Tyr Arg Gly Arg Lys Asn Leu
        1700                1705                1710
```

-continued

```
gtg tct gat tcg gag tgc aat cca aaa act aag ctc aac tct gtt gcc    5184
Val Ser Asp Ser Glu Cys Asn Pro Lys Thr Lys Leu Asn Ser Val Ala
        1715                1720                1725 aac tgt ttc cca gtg gct tgt cca gct tat aga tgg aat gtt act cca    5232
Asn Cys Phe Pro Val Ala Cys Pro Ala Tyr Arg Trp Asn Val Thr Pro
    1730                1735                1740 tgg agc aag tgc aaa gat gag tgt gct cga gga caa aag caa act cgt    5280
Trp Ser Lys Cys Lys Asp Glu Cys Ala Arg Gly Gln Lys Gln Thr Arg
1745                1750                1755                1760 cgg gtg cac tgt ata agc act tct ggt aaa cga gca gct cca cga atg    5328
Arg Val His Cys Ile Ser Thr Ser Gly Lys Arg Ala Ala Pro Arg Met
            1765                1770                1775 tgt gaa ttg gct cgt gca cca act tcg atc aga gag tgc gat aca tca    5376
Cys Glu Leu Ala Arg Ala Pro Thr Ser Ile Arg Glu Cys Asp Thr Ser
                1780                1785                1790 aat tgt cca tat gag tgg gtg cca gga gat tgg caa acg tgt tca aag    5424
Asn Cys Pro Tyr Glu Trp Val Pro Gly Asp Trp Gln Thr Cys Ser Lys
        1795                1800                1805 tca tgt gga gaa gga gta cag aca cga gaa gtc aga tgt cgt aga aag    5472
Ser Cys Gly Glu Gly Val Gln Thr Arg Glu Val Arg Cys Arg Arg Lys
    1810                1815                1820 att aat ttt aac tca acc att cca att ata ttt atg ctc gaa gat gaa    5520
Ile Asn Phe Asn Ser Thr Ile Pro Ile Ile Phe Met Leu Glu Asp Glu
1825                1830                1835                1840 cca gct gta cca aaa gag aaa tgt gaa ctt ttc cca aaa cca aat gaa    5568
Pro Ala Val Pro Lys Glu Lys Cys Glu Leu Phe Pro Lys Pro Asn Glu
            1845                1850                1855 tct caa acg tgc gaa ctt aac cca tgc gat tcg gaa ttc aaa tgg agt    5616
Ser Gln Thr Cys Glu Leu Asn Pro Cys Asp Ser Glu Phe Lys Trp Ser
                1860                1865                1870 ttc gga cca tgg ggt gaa tgc tcg aaa aat tgc ggt caa ggt att cga    5664
Phe Gly Pro Trp Gly Glu Cys Ser Lys Asn Cys Gly Gln Gly Ile Arg
        1875                1880                1885 cgt cga cgt gtc aag tgt gtg gcc aat gat ggt cgt cga gtt gaa cga    5712
Arg Arg Arg Val Lys Cys Val Ala Asn Asp Gly Arg Arg Val Glu Arg
    1890                1895                1900 gtc aag tgt acc aca aag aaa cca cgt cga act caa tat tgt ttt gaa    5760
Val Lys Cys Thr Thr Lys Lys Pro Arg Arg Thr Gln Tyr Cys Phe Glu
1905                1910                1915                1920 aga aat tgc ctt ccg tca act tgt cag gag ctt aaa tct cag aat gtt    5808
Arg Asn Cys Leu Pro Ser Thr Cys Gln Glu Leu Lys Ser Gln Asn Val
            1925                1930                1935 aag gct aaa gat gga aat tac act att ctt ctt gac gga ttc act att    5856
Lys Ala Lys Asp Gly Asn Tyr Thr Ile Leu Leu Asp Gly Phe Thr Ile
                1940                1945                1950 gaa att tat tgt cat cga atg aat tca acc att cct aaa gct tat ttg    5904
Glu Ile Tyr Cys His Arg Met Asn Ser Thr Ile Pro Lys Ala Tyr Leu
        1955                1960                1965 aac gtt aat cca aga acc aat ttt gca gag gtt tat gga aaa aaa tta    5952
Asn Val Asn Pro Arg Thr Asn Phe Ala Glu Val Tyr Gly Lys Lys Leu
    1970                1975                1980 ata tac cct cat act tgc cca ttt aat ggt gat cgt aat gat tca tgc    6000
Ile Tyr Pro His Thr Cys Pro Phe Asn Gly Asp Arg Asn Asp Ser Cys
1985                1990                1995                2000 cat tgt tca gaa gac ggc gat gca agt gct gga ttg acg aga ttc aat    6048
His Cys Ser Glu Asp Gly Asp Ala Ser Ala Gly Leu Thr Arg Phe Asn
            2005                2010                2015 aaa gtt cga ata gat ttg ttg aat aga aag ttc cat ctg gcg gat tat    6096
Lys Val Arg Ile Asp Leu Leu Asn Arg Lys Phe His Leu Ala Asp Tyr
```

```
aca ttt gca aaa cga gaa tat ggt gtt cat gtg cca tat ggt act gcc    6144
Thr Phe Ala Lys Arg Glu Tyr Gly Val His Val Pro Tyr Gly Thr Ala
        2035                2040                2045 ggt gat tgc tac agt atg aaa gat tgt cca cag gga ata ttc tca att    6192
Gly Asp Cys Tyr Ser Met Lys Asp Cys Pro Gln Gly Ile Phe Ser Ile
    2050                2055                2060 gat tta aaa tct gct ggt ctg aaa tta gtt gac gat ctg aat tgg gag    6240
Asp Leu Lys Ser Ala Gly Leu Lys Leu Val Asp Asp Leu Asn Trp Glu
2065                2070                2075                2080 gat caa ggt cat cga aca tcc tct cga atc gat cgt ttt tat aac aat    6288
Asp Gln Gly His Arg Thr Ser Ser Arg Ile Asp Arg Phe Tyr Asn Asn
            2085                2090                2095 gca aaa gtt att ggt cac tgt ggt ggt ttt tgt gga aaa tgc tct cct    6336
Ala Lys Val Ile Gly His Cys Gly Gly Phe Cys Gly Lys Cys Ser Pro
                2100                2105                2110 gag cgg tac aaa gga cta atc ttt gaa gtt aat aca aaa tta tta aat    6384
Glu Arg Tyr Lys Gly Leu Ile Phe Glu Val Asn Thr Lys Leu Leu Asn
            2115                2120                2125 cat gtg aaa aat ggt gga cac att gat gat gaa ttg gat gat gat ggt    6432
His Val Lys Asn Gly Gly His Ile Asp Asp Glu Leu Asp Asp Asp Gly
2130                2135                2140 ttc tct ggt gac atg gat taatttttc gatacctaaa agtgtcaaaa            6480
Phe Ser Gly Asp Met Asp
2145            2150 tctcgtatga atctctactt ctctggtctc ttatttcaag ttttttgattc ttttcttttt  6540 tttagttttt aatagcatta cttcgaattt attgtcattc cctcaatcac ctaacactag  6600
gttttctaca tagtatgttc cttgaaaatg tttcatgatc aaaggttacg gtactttg    6659

<210> SEQ ID NO 2
<211> LENGTH: 2150
<212> TYPE: PRT
<213> ORGANISM: Caenorhabditis elegans

<400> SEQUENCE: 2

Met Arg Ser Ile Gly Gly Ser Phe His Leu Leu Gln Pro Val Val Ala
 1               5                  10                  15

Ala Leu Ile Leu Leu Val Val Cys Leu Val Tyr Ala Leu Gln Ser Gly
            20                  25                  30

Ser Gly Thr Ile Ser Glu Phe Ser Ser Asp Val Leu Phe Ser Arg Ala
        35                  40                  45

Lys Tyr Ser Gly Val Pro Val His His Ser Arg Trp Arg Gln Asp Ala
    50                  55                  60

Gly Ile His Val Ile Asp Ser His Ile Val Arg Arg Asp Ser Tyr
65                  70                  75                  80

Gly Arg Arg Gly Lys Arg Asp Val Thr Ser Thr Asp Arg Arg Arg
                85                  90                  95

Leu Gln Gly Val Ala Arg Asp Cys Gly His Ala Cys His Leu Arg Leu
            100                 105                 110

Arg Ser Asp Asp Ala Val Tyr Ile Val His Leu His Arg Trp Asn Gln
        115                 120                 125

Ile Pro Asp Ser His Asn Lys Ser Val Pro His Phe Ser Asn Ser Asn
    130                 135                 140

Phe Ala Pro Met Val Leu Tyr Leu Asp Ser Glu Glu Val Arg Gly
145                 150                 155                 160

Gly Met Ser Arg Thr Asp Pro Asp Cys Ile Tyr Arg Ala His Val Lys
```

-continued

```
                165                 170                 175
Gly Val His Gln His Ser Ile Val Asn Leu Cys Asp Ser Glu Asp Gly
                    180                 185                 190

Leu Tyr Gly Met Leu Ala Leu Pro Ser Gly Ile His Thr Val Glu Pro
            195                 200                 205

Ile Ile Ser Gly Asn Gly Thr Glu His Asp Gly Ala Ser Arg His Arg
        210                 215                 220

Gln His Leu Val Arg Lys Phe Asp Pro Met His Phe Lys Ser Phe Asp
225                 230                 235                 240

His Leu Asn Ser Thr Ser Val Asn Glu Thr Glu Thr Val Ala Thr
                245                 250                 255

Trp Gln Asp Gln Trp Glu Asp Val Ile Glu Arg Lys Ala Arg Ser Arg
                260                 265                 270

Arg Ala Ala Asn Ser Trp Asp His Tyr Val Glu Val Leu Val Ala
            275                 280                 285

Asp Thr Lys Met Tyr Glu Tyr His Gly Arg Ser Leu Glu Asp Tyr Val
        290                 295                 300

Leu Thr Leu Phe Ser Thr Val Ala Ser Ile Tyr Arg His Gln Ser Leu
305                 310                 315                 320

Arg Ala Ser Ile Asn Val Val Val Lys Leu Ile Val Leu Lys Thr
                325                 330                 335

Glu Asn Ala Gly Pro Arg Ile Thr Gln Asn Ala Gln Gln Thr Leu Gln
                340                 345                 350

Asp Phe Cys Arg Trp Gln Gln Tyr Tyr Asn Asp Pro Asp Ser Ser
            355                 360                 365

Val Gln His His Asp Val Ala Ile Leu Leu Thr Arg Lys Asp Ile Cys
        370                 375                 380

Arg Ser Gln Gly Lys Cys Asp Thr Leu Gly Leu Ala Glu Leu Gly Thr
385                 390                 395                 400

Met Cys Asp Met Gln Lys Ser Cys Ala Ile Ile Glu Asp Asn Gly Leu
                405                 410                 415

Ser Ala Ala Phe Thr Ile Ala His Glu Leu Gly His Val Phe Ser Ile
            420                 425                 430

Pro His Asp Asp Glu Arg Lys Cys Ser Thr Tyr Met Pro Val Asn Lys
        435                 440                 445

Asn Asn Phe His Ile Met Ala Pro Thr Leu Glu Tyr Asn Thr His Pro
450                 455                 460

Trp Ser Trp Ser Pro Cys Ser Ala Gly Met Leu Glu Arg Phe Leu Glu
465                 470                 475                 480

Asn Asn Arg Gly Gln Thr Gln Cys Leu Phe Asp Gln Pro Val Glu Arg
                485                 490                 495

Arg Tyr Tyr Glu Asp Val Phe Val Arg Asp Glu Pro Gly Lys Lys Tyr
            500                 505                 510

Asp Ala His Gln Gln Cys Lys Phe Val Phe Gly Pro Ala Ser Glu Leu
        515                 520                 525

Cys Pro Tyr Met Pro Thr Cys Arg Arg Leu Trp Cys Ala Thr Phe Tyr
    530                 535                 540

Gly Ser Gln Met Gly Cys Arg Thr Gln His Met Pro Trp Ala Asp Gly
545                 550                 555                 560

Thr Pro Cys Asp Glu Ser Arg Ser Met Phe Cys His His Gly Ala Cys
                565                 570                 575

Val Arg Leu Ala Pro Glu Ser Leu Thr Lys Ile Asp Gly Gln Trp Gly
            580                 585                 590
```

-continued

```
Asp Trp Arg Ser Trp Gly Glu Cys Ser Arg Thr Cys Gly Gly Val
        595                 600                 605
Gln Lys Gly Leu Arg Asp Cys Asp Ser Pro Lys Pro Arg Asn Gly Gly
    610                 615                 620
Lys Tyr Cys Val Gly Gln Arg Glu Arg Tyr Arg Ser Cys Asn Thr Gln
625                 630                 635                 640
Glu Cys Pro Trp Asp Thr Gln Pro Tyr Arg Glu Val Gln Cys Ser Glu
                    645                 650                 655
Phe Asn Asn Lys Asp Ile Gly Ile Gln Gly Val Ala Ser Thr Asn Thr
                660                 665                 670
His Trp Val Pro Lys Tyr Ala Asn Val Ala Pro Asn Glu Arg Cys Lys
            675                 680                 685
Leu Tyr Cys Arg Leu Ser Gly Ser Ala Ala Phe Tyr Leu Leu Arg Asp
        690                 695                 700
Lys Val Val Asp Gly Thr Pro Cys Asp Arg Asn Gly Asp Asp Ile Cys
705                 710                 715                 720
Val Ala Gly Ala Cys Met Pro Ala Gly Cys Asp His Gln Leu His Ser
                    725                 730                 735
Thr Leu Arg Arg Asp Lys Cys Gly Val Cys Gly Gly Asp Asp Ser Ser
                740                 745                 750
Cys Lys Val Val Lys Gly Thr Phe Asn Glu Gln Gly Thr Phe Gly Tyr
            755                 760                 765
Asn Glu Val Met Lys Ile Pro Ala Gly Ser Ala Asn Ile Asp Ile Arg
        770                 775                 780
Gln Lys Gly Tyr Asn Asn Met Lys Glu Asp Asp Asn Tyr Leu Ser Leu
785                 790                 795                 800
Arg Ala Ala Asn Gly Glu Phe Leu Leu Asn Gly His Phe Gln Val Ser
                    805                 810                 815
Leu Ala Arg Gln Gln Ile Ala Phe Gln Asp Thr Val Leu Glu Tyr Ser
                820                 825                 830
Gly Ser Asp Ala Ile Ile Glu Arg Ile Asn Gly Thr Gly Pro Ile Arg
            835                 840                 845
Ser Asp Ile Tyr Val His Val Leu Ser Val Gly Ser His Pro Pro Asp
        850                 855                 860
Ile Ser Tyr Glu Tyr Met Thr Ala Val Pro Asn Ala Val Ile Arg
865                 870                 875                 880
Pro Ile Ser Ser Ala Leu Tyr Leu Trp Arg Val Thr Asp Thr Trp Thr
                    885                 890                 895
Glu Cys Asp Arg Ala Cys Arg Gly Gln Gln Ser Gln Lys Leu Met Cys
                900                 905                 910
Leu Asp Met Ser Thr His Arg Gln Ser His Asp Arg Asn Cys Gln Asn
            915                 920                 925
Val Leu Lys Pro Lys Gln Ala Thr Arg Met Cys Asn Ile Asp Cys Ser
        930                 935                 940
Thr Arg Trp Ile Thr Glu Asp Val Ser Ser Cys Ser Ala Lys Cys Gly
945                 950                 955                 960
Ser Gly Gln Lys Arg Gln Arg Val Ser Cys Val Lys Met Glu Gly Asp
                    965                 970                 975
Arg Gln Thr Pro Ala Ser Glu His Leu Cys Asp Arg Asn Ser Lys Pro
                980                 985                 990
Ser Asp Ile Ala Ser Cys Tyr Ile Asp Cys Ser Gly Arg Lys Trp Asn
            995                 1000                1005
```

-continued

```
Tyr Gly Glu Trp Thr Ser Cys Ser Glu Thr Cys Gly Ser Asn Gly Lys
    1010                1015                1020
Met His Arg Lys Ser Tyr Cys Val Asp Asp Ser Asn Arg Arg Val Asp
1025                1030                1035                1040
Glu Ser Leu Cys Gly Arg Glu Gln Lys Glu Ala Thr Glu Arg Glu Cys
                1045                1050                1055
Asn Arg Ile Pro Cys Pro Arg Trp Val Tyr Gly His Trp Ser Glu Cys
            1060                1065                1070
Ser Arg Ser Cys Asp Gly Gly Val Lys Met Arg His Ala Gln Cys Leu
        1075                1080                1085
Asp Ala Ala Asp Arg Glu Thr His Thr Ser Arg Cys Gly Pro Ala Gln
    1090                1095                1100
Thr Gln Glu His Cys Asn Glu His Ala Cys Thr Trp Trp Gln Phe Gly
1105                1110                1115                1120
Val Trp Ser Asp Cys Ser Ala Lys Cys Gly Asp Gly Val Gln Tyr Arg
                1125                1130                1135
Asp Ala Asn Cys Thr Asp Arg His Arg Ser Val Leu Pro Glu His Arg
            1140                1145                1150
Cys Leu Lys Met Glu Lys Ile Ile Thr Lys Pro Cys His Arg Glu Ser
        1155                1160                1165
Cys Pro Lys Tyr Lys Leu Gly Glu Trp Ser Gln Cys Ser Val Ser Cys
    1170                1175                1180
Glu Asp Gly Trp Ser Ser Arg Arg Val Ser Cys Val Ser Gly Asn Gly
1185                1190                1195                1200
Thr Glu Val Asp Met Ser Leu Cys Gly Thr Ala Ser Asp Arg Pro Ala
                1205                1210                1215
Ser His Gln Thr Cys Asn Leu Gly Thr Cys Pro Phe Trp Arg Asn Thr
            1220                1225                1230
Asp Trp Ser Ala Cys Ser Val Ser Cys Gly Ile Gly His Arg Glu Arg
        1235                1240                1245
Thr Thr Glu Cys Ile Tyr Arg Glu Gln Ser Val Asp Ala Ser Phe Cys
    1250                1255                1260
Gly Asp Thr Lys Met Pro Glu Thr Ser Gln Thr Cys His Leu Leu Pro
1265                1270                1275                1280
Cys Thr Ser Trp Lys Pro Ser His Trp Ser Pro Cys Ser Val Thr Cys
                1285                1290                1295
Gly Ser Gly Ile Gln Thr Arg Ser Val Ser Cys Thr Arg Gly Ser Glu
            1300                1305                1310
Gly Thr Ile Val Asp Glu Tyr Phe Cys Asp Arg Asn Thr Arg Pro Arg
        1315                1320                1325
Leu Lys Lys Thr Cys Glu Lys Asp Thr Cys Asp Gly Pro Arg Val Leu
    1330                1335                1340
Gln Lys Leu Gln Ala Asp Val Pro Pro Ile Arg Trp Ala Thr Gly Pro
1345                1350                1355                1360
Trp Thr Ala Cys Ser Ala Thr Cys Gly Asn Gly Thr Gln Arg Arg Leu
                1365                1370                1375
Leu Lys Cys Arg Asp His Val Arg Asp Leu Pro Asp Glu Tyr Cys Asn
            1380                1385                1390
His Leu Asp Lys Glu Val Ser Thr Arg Asn Cys Arg Leu Arg Asp Cys
        1395                1400                1405
Ser Tyr Trp Lys Met Ala Glu Trp Glu Glu Cys Pro Ala Thr Cys Gly
    1410                1415                1420
Thr His Val Gln Gln Ser Arg Asn Val Thr Cys Val Ser Ala Glu Asp
```

```
                     1425               1430                1435                1440

Gly Gly Arg Thr Ile Leu Lys Asp Val Asp Cys Asp Val Gln Lys Arg
                         1445                1450                1455

Pro Thr Ser Ala Arg Asn Cys Arg Leu Glu Pro Cys Pro Lys Gly Glu
             1460                1465                1470

Glu His Ile Gly Ser Trp Ile Ile Gly Asp Trp Ser Lys Cys Ser Ala
             1475                1480                1485

Ser Cys Gly Gly Gly Trp Arg Arg Arg Ser Val Ser Cys Thr Ser Ser
             1490                1495                1500

Ser Cys Asp Glu Thr Arg Lys Pro Lys Met Phe Asp Lys Cys Asn Glu
     1505                1510                1515                1520

Glu Leu Cys Pro Pro Leu Thr Asn Asn Ser Trp Gln Ile Ser Pro Trp
                     1525                1530                1535

Thr His Cys Ser Val Ser Cys Gly Gly Gly Val Gln Arg Arg Lys Ile
                         1540                1545                1550

Trp Cys Glu Asp Val Leu Ser Gly Arg Lys Gln Asp Asp Ile Glu Cys
                     1555                1560                1565

Ser Glu Ile Lys Pro Arg Glu Gln Arg Asp Cys Glu Met Pro Pro Cys
             1570                1575                1580

Arg Ser His Tyr His Asn Lys Thr Ser Ser Ala Ser Met Thr Ser Leu
     1585                1590                1595                1600

Ser Ser Ser Asn Ser Asn Thr Thr Ser Ser Ala Ser Ala Ser Ser Leu
                     1605                1610                1615

Pro Ile Leu Pro Pro Val Val Ser Trp Gln Thr Ser Ala Trp Ser Ala
                 1620                1625                1630

Cys Ser Ala Lys Cys Gly Arg Gly Thr Lys Arg Arg Val Val Glu Cys
                     1635                1640                1645

Val Asn Pro Ser Leu Asn Val Thr Val Ala Ser Thr Glu Cys Asp Gln
             1650                1655                1660

Thr Lys Lys Pro Val Glu Glu Val Arg Cys Arg Thr Lys His Cys Pro
     1665                1670                1675                1680

Arg Trp Lys Thr Thr Thr Trp Ser Ser Cys Ser Val Thr Cys Gly Arg
                 1685                1690                1695

Gly Ile Arg Arg Arg Glu Val Gln Cys Tyr Arg Gly Arg Lys Asn Leu
                 1700                1705                1710

Val Ser Asp Ser Glu Cys Asn Pro Lys Thr Lys Leu Asn Ser Val Ala
                 1715                1720                1725

Asn Cys Phe Pro Val Ala Cys Pro Ala Tyr Arg Trp Asn Val Thr Pro
                 1730                1735                1740

Trp Ser Lys Cys Lys Asp Glu Cys Ala Arg Gly Gln Lys Gln Thr Arg
     1745                1750                1755                1760

Arg Val His Cys Ile Ser Thr Ser Gly Lys Arg Ala Ala Pro Arg Met
                     1765                1770                1775

Cys Glu Leu Ala Arg Ala Pro Thr Ser Ile Arg Glu Cys Asp Thr Ser
                 1780                1785                1790

Asn Cys Pro Tyr Glu Trp Val Pro Gly Asp Trp Gln Thr Cys Ser Lys
             1795                1800                1805

Ser Cys Gly Glu Gly Val Gln Thr Arg Glu Val Arg Cys Arg Arg Lys
         1810                1815                1820

Ile Asn Phe Asn Ser Thr Ile Pro Ile Ile Phe Met Leu Glu Asp Glu
     1825                1830                1835                1840

Pro Ala Val Pro Lys Glu Lys Cys Glu Leu Phe Pro Lys Pro Asn Glu
                 1845                1850                1855
```

Ser Gln Thr Cys Glu Leu Asn Pro Cys Asp Ser Glu Phe Lys Trp Ser
        1860                1865                1870

Phe Gly Pro Trp Gly Glu Cys Ser Lys Asn Cys Gly Gln Gly Ile Arg
    1875                1880                1885

Arg Arg Arg Val Lys Cys Val Ala Asn Asp Gly Arg Arg Val Glu Arg
    1890                1895                1900

Val Lys Cys Thr Thr Lys Lys Pro Arg Arg Thr Gln Tyr Cys Phe Glu
1905                1910                1915                1920

Arg Asn Cys Leu Pro Ser Thr Cys Gln Glu Leu Lys Ser Gln Asn Val
            1925                1930                1935

Lys Ala Lys Asp Gly Asn Tyr Thr Ile Leu Leu Asp Gly Phe Thr Ile
        1940                1945                1950

Glu Ile Tyr Cys His Arg Met Asn Ser Thr Ile Pro Lys Ala Tyr Leu
    1955                1960                1965

Asn Val Asn Pro Arg Thr Asn Phe Ala Glu Val Tyr Gly Lys Lys Leu
        1970                1975                1980

Ile Tyr Pro His Thr Cys Pro Phe Asn Gly Asp Arg Asn Asp Ser Cys
1985                1990                1995                2000

His Cys Ser Glu Asp Gly Asp Ala Ser Ala Gly Leu Thr Arg Phe Asn
            2005                2010                2015

Lys Val Arg Ile Asp Leu Leu Asn Arg Lys Phe His Leu Ala Asp Tyr
        2020                2025                2030

Thr Phe Ala Lys Arg Glu Tyr Gly Val His Val Pro Tyr Gly Thr Ala
        2035                2040                2045

Gly Asp Cys Tyr Ser Met Lys Asp Cys Pro Gln Gly Ile Phe Ser Ile
    2050                2055                2060

Asp Leu Lys Ser Ala Gly Leu Lys Leu Val Asp Asp Leu Asn Trp Glu
2065                2070                2075                2080

Asp Gln Gly His Arg Thr Ser Ser Arg Ile Asp Arg Phe Tyr Asn Asn
            2085                2090                2095

Ala Lys Val Ile Gly His Cys Gly Gly Phe Cys Gly Lys Cys Ser Pro
        2100                2105                2110

Glu Arg Tyr Lys Gly Leu Ile Phe Glu Val Asn Thr Lys Leu Leu Asn
    2115                2120                2125

His Val Lys Asn Gly Gly His Ile Asp Asp Glu Leu Asp Asp Asp Gly
    2130                2135                2140

Phe Ser Gly Asp Met Asp
2145                2150

<210> SEQ ID NO 3
<211> LENGTH: 76
<212> TYPE: PRT
<213> ORGANISM: Artificial Sequence
<220> FEATURE:
<221> NAME/KEY: VARIANT
<222> LOCATION: (2)..(6)
<223> OTHER INFORMATION: Can be any amino acid; can have only 4
      instead of 5 amino acids.
<221> NAME/KEY: VARIANT
<222> LOCATION: (8)..(9)
<223> OTHER INFORMATION: Can be any amino acid.
<221> NAME/KEY: VARIANT
<222> LOCATION: (12)..(13)
<223> OTHER INFORMATION: Can be any amino acid.
<221> NAME/KEY: VARIANT
<222> LOCATION: (16)..(20)
<223> OTHER INFORMATION: Can be any amino acid; can have only 4
      instead of 5 amino acids.
<221> NAME/KEY: VARIANT

```
<222> LOCATION: (23)..(25)
<223> OTHER INFORMATION: Can be any amino acid.
<221> NAME/KEY: VARIANT
<222> LOCATION: (27)..(29)
<223> OTHER INFORMATION: Can be any amino acid.
<221> NAME/KEY: VARIANT
<222> LOCATION: (31)..(57)
<223> OTHER INFORMATION: Can be any amino acid; can have as few
      as 4 or as many as 27 amino acids.
<221> NAME/KEY: VARIANT
<222> LOCATION: (59)..(70)
<223> OTHER INFORMATION: Can be any amino acid; can have as few as
      8 or as many as 12 amino acids.
<221> NAME/KEY: VARIANT
<222> LOCATION: (72)..(75)
<223> OTHER INFORMATION: Can be any amino acid; can have only 3
      instead of 4 amino acids.
<223> OTHER INFORMATION: Description of Artificial Sequence:
      consensus sequence for TSPt1-like repeats
<221> NAME/KEY: VARIANT
<222> LOCATION: (21)
<223> OTHER INFORMATION: Can be any amino acid.

<400> SEQUENCE: 3

Trp Xaa Xaa Xaa Xaa Trp Xaa Xaa Cys Ser Xaa Xaa Cys Gly Xaa
 1               5                  10                  15

Xaa Xaa Xaa Xaa Xaa Gly Xaa Xaa Xaa Arg Xaa Xaa Xaa Cys Xaa Xaa
                20                  25                  30

Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Cys Xaa Xaa Xaa Xaa Xaa
         50                  55                  60

Xaa Xaa Xaa Xaa Xaa Xaa Cys Xaa Xaa Xaa Xaa Cys
 65                  70                  75

<210> SEQ ID NO 4
<211> LENGTH: 950
<212> TYPE: PRT
<213> ORGANISM: Murine

<400> SEQUENCE: 4

Met Gly Asp Val Gln Arg Ala Ala Arg Ser Arg Gly Ser Leu Ser Ala
 1               5                  10                  15

His Met Leu Leu Leu Leu Ala Ser Ile Thr Met Leu Leu Cys Ala
                20                  25                  30

Arg Gly Ala His Gly Arg Pro Thr Glu Glu Asp Glu Glu Leu Val Leu
         35                  40                  45

Pro Ser Leu Glu Arg Ala Pro Gly His Asp Ser Thr Thr Arg Leu
 50                  55                  60

Arg Leu Asp Ala Phe Gly Gln Gln Leu His Leu Lys Leu Gln Pro Asp
 65                  70                  75                  80

Ser Gly Phe Leu Ala Pro Gly Phe Thr Leu Gln Thr Val Gly Arg Ser
                85                  90                  95

Pro Gly Ser Glu Ala Gln His Leu Asp Pro Thr Gly Asp Leu Ala His
                100                 105                 110

Cys Phe Tyr Ser Gly Thr Val Asn Gly Asp Pro Gly Ser Ala Ala Ala
            115                 120                 125

Leu Ser Leu Cys Glu Gly Val Arg Gly Ala Phe Tyr Leu Gln Gly Glu
        130                 135                 140

Glu Phe Phe Ile Gln Pro Ala Pro Gly Val Ala Thr Glu Arg Leu Ala
145                 150                 155                 160

Pro Ala Val Pro Glu Glu Glu Ser Ser Ala Arg Pro Gln Phe His Ile
```

-continued

```
                165                 170                 175
Leu Arg Arg Arg Arg Gly Ser Gly Gly Ala Lys Cys Gly Val Met
                180                 185                 190
Asp Asp Glu Thr Leu Pro Thr Ser Asp Ser Arg Pro Glu Ser Gln Asn
            195                 200                 205
Thr Arg Asn Gln Trp Pro Val Arg Asp Pro Thr Pro Gln Asp Ala Gly
        210                 215                 220
Lys Pro Ser Gly Pro Gly Ser Ile Arg Lys Arg Phe Val Ser Ser
225                 230                 235                 240
Pro Arg Tyr Val Glu Thr Met Leu Val Ala Asp Gln Ser Met Ala Asp
                245                 250                 255
Phe His Gly Ser Gly Leu Lys His Tyr Leu Leu Thr Leu Phe Ser Val
                260                 265                 270
Ala Ala Arg Phe Tyr Lys His Pro Ser Ile Arg Asn Ser Ile Ser Leu
            275                 280                 285
Val Val Lys Ile Leu Val Ile Tyr Glu Glu Gln Lys Gly Pro Glu
        290                 295                 300
Val Thr Ser Asn Ala Ala Leu Thr Leu Arg Asn Phe Cys Asn Trp Gln
305                 310                 315                 320
Lys Gln His Asn Ser Pro Ser Asp Arg Asp Pro Glu His Tyr Asp Thr
                325                 330                 335
Ala Ile Leu Phe Thr Arg Gln Asp Leu Cys Gly Ser His Thr Cys Asp
                340                 345                 350
Thr Leu Gly Met Ala Asp Val Gly Thr Val Cys Asp Pro Ser Arg Ser
            355                 360                 365
Cys Ser Val Ile Glu Asp Gly Leu Gln Ala Ala Phe Thr Thr Ala
        370                 375                 380
His Glu Leu Gly His Val Phe Asn Met Pro His Asp Asp Ala Lys His
385                 390                 395                 400
Cys Ala Ser Leu Asn Gly Val Thr Gly Asp Ser His Leu Met Ala Ser
                405                 410                 415
Met Leu Ser Ser Leu Asp His Ser Gln Pro Trp Ser Pro Cys Ser Ala
                420                 425                 430
Tyr Met Val Thr Ser Phe Leu Asp Asn Gly His Gly Glu Cys Leu Met
            435                 440                 445
Asp Lys Pro Gln Asn Pro Ile Lys Leu Pro Ser Asp Leu Pro Gly Thr
        450                 455                 460
Leu Tyr Asp Ala Asn Arg Gln Cys Gln Phe Thr Phe Gly Glu Glu Ser
465                 470                 475                 480
Lys His Cys Pro Asp Ala Ala Ser Thr Cys Thr Thr Leu Trp Cys Thr
                485                 490                 495
Gly Thr Ser Gly Gly Leu Leu Val Cys Gln Thr Lys His Phe Pro Trp
            500                 505                 510
Ala Asp Gly Thr Ser Cys Gly Glu Gly Lys Trp Cys Val Ser Gly Lys
            515                 520                 525
Cys Val Asn Lys Thr Asp Met Lys His Phe Ala Thr Pro Val His Gly
        530                 535                 540
Ser Trp Gly Pro Trp Gly Pro Trp Gly Asp Cys Ser Arg Thr Cys Gly
545                 550                 555                 560
Gly Gly Val Gln Tyr Thr Met Arg Glu Cys Asp Asn Pro Val Pro Lys
                565                 570                 575
Asn Gly Gly Lys Tyr Cys Glu Gly Lys Arg Val Arg Tyr Arg Ser Cys
            580                 585                 590
```

```
Asn Ile Glu Asp Cys Pro Asp Asn Asn Gly Lys Thr Phe Arg Glu Glu
            595                 600                 605

Gln Cys Glu Ala His Asn Glu Phe Ser Lys Ala Ser Phe Gly Asn Glu
        610                 615                 620

Pro Thr Val Glu Trp Thr Pro Lys Tyr Ala Gly Val Ser Pro Lys Asp
625                 630                 635                 640

Arg Cys Lys Leu Thr Cys Glu Ala Lys Gly Ile Gly Tyr Phe Phe Val
                645                 650                 655

Leu Gln Pro Lys Val Val Asp Gly Thr Pro Cys Ser Pro Asp Ser Thr
            660                 665                 670

Ser Val Cys Val Gln Gly Gln Cys Val Lys Ala Gly Cys Asp Arg Ile
        675                 680                 685

Ile Asp Ser Lys Lys Phe Asp Lys Cys Gly Val Cys Gly Gly Asn
690                 695                 700

Gly Ser Thr Cys Lys Lys Met Ser Gly Ile Val Thr Ser Thr Arg Pro
705                 710                 715                 720

Gly Tyr His Asp Ile Val Thr Ile Pro Ala Gly Ala Thr Asn Ile Glu
                725                 730                 735

Val Lys His Arg Asn Gln Arg Gly Ser Arg Asn Asn Gly Ser Phe Leu
            740                 745                 750

Ala Ile Arg Ala Ala Asp Gly Thr Tyr Ile Leu Asn Gly Asn Phe Thr
        755                 760                 765

Leu Ser Thr Leu Glu Gln Asp Leu Thr Tyr Lys Gly Thr Val Leu Arg
        770                 775                 780

Tyr Ser Gly Ser Ser Ala Ala Leu Glu Arg Ile Arg Ser Phe Ser Pro
785                 790                 795                 800

Leu Lys Glu Pro Leu Thr Ile Gln Val Leu Met Val Gly His Ala Leu
                805                 810                 815

Arg Pro Lys Ile Lys Phe Thr Tyr Phe Met Lys Lys Thr Glu Ser
            820                 825                 830

Phe Asn Ala Ile Pro Thr Phe Ser Glu Trp Val Ile Glu Glu Trp Gly
        835                 840                 845

Glu Cys Ser Lys Thr Cys Gly Ser Gly Trp Gln Arg Arg Val Val Gln
850                 855                 860

Cys Arg Asp Ile Asn Gly His Pro Ala Ser Glu Cys Ala Lys Glu Val
865                 870                 875                 880

Lys Pro Ala Ser Thr Arg Pro Cys Ala Asp Leu Pro Cys Pro His Trp
                885                 890                 895

Gln Val Gly Asp Trp Ser Pro Cys Ser Lys Thr Cys Gly Lys Gly Tyr
            900                 905                 910

Lys Lys Arg Thr Leu Lys Cys Val Ser His Asp Gly Gly Val Leu Ser
        915                 920                 925

Asn Glu Ser Cys Asp Pro Leu Lys Pro Lys His Tyr Ile Asp Phe
        930                 935                 940

Cys Thr Leu Thr Gln Cys
945                 950

<210> SEQ ID NO 5
<211> LENGTH: 969
<212> TYPE: PRT
<213> ORGANISM: Bovine

<400> SEQUENCE: 5

Met Asp Pro Pro Ala Gly Ala Ala Gly Arg Leu Leu Cys Pro Ala Leu
```

-continued

```
  1               5                    10                   15
Leu Leu Leu Leu Leu Leu Pro Leu Pro Ala Asp Ala Arg Leu Ala Ala
             20                  25                 30
Ala Ala Ala Asp Pro Pro Gly Gly Pro Gln Gly His Gly Ala Glu Arg
         35                 40                 45
Ile Leu Ala Val Pro Val Arg Thr Asp Ala Gln Gly Arg Leu Val Ser
     50                 55                 60
His Val Val Ser Ala Ala Thr Ala Pro Ala Gly Val Arg Thr Arg Arg
 65                 70                 75                 80
Ala Ala Pro Ala Gln Ile Pro Gly Leu Ser Gly Ser Glu Glu Asp
                 85                 90                 95
Pro Gly Gly Arg Leu Phe Tyr Asn Val Thr Val Phe Gly Arg Asp Leu
             100                105                110
His Leu Arg Leu Arg Pro Asn Ala Arg Leu Val Ala Pro Gly Ala Thr
         115                120                125
Val Glu Trp Gln Gly Glu Ser Gly Ala Thr Arg Val Glu Pro Leu Leu
     130                135                140
Gly Thr Cys Leu Tyr Val Gly Asp Val Ala Gly Leu Ala Glu Ser Ser
145                150                155                160
Ser Val Ala Leu Ser Asn Cys Asp Gly Leu Ala Gly Leu Ile Arg Met
             165                170                175
Glu Glu Glu Glu Phe Phe Ile Glu Pro Leu Glu Lys Gly Leu Ala Ala
         180                185                190
Lys Glu Ala Glu Gln Gly Arg Val His Val Val Tyr His Arg Pro Thr
     195                200                205
Thr Ser Arg Pro Pro Pro Leu Gly Gly Pro Gln Ala Leu Asp Thr Gly
     210                215                220
Ile Ser Ala Asp Ser Leu Asp Ser Leu Ser Arg Ala Leu Gly Val Leu
225                230                235                240
Glu Glu Arg Val Asn Ser Ser Arg Arg Met Arg Arg His Ala Ala
             245                250                255
Asp Asp Asp Tyr Asn Ile Glu Val Leu Leu Gly Val Asp Ser Val
         260                265                270
Val Gln Phe His Gly Thr Glu His Val Gln Lys Tyr Leu Leu Thr Leu
     275                280                285
Met Asn Ile Val Asn Glu Ile Tyr His Asp Glu Ser Leu Gly Ala His
     290                295                300
Ile Asn Val Val Leu Val Arg Ile Ile Leu Leu Ser Tyr Gly Lys Ser
305                310                315                320
Met Ser Leu Ile Glu Ile Gly Asn Pro Ser Gln Ser Leu Glu Asn Val
             325                330                335
Cys Arg Trp Ala Tyr Leu Gln Gln Lys Pro Asp Thr Asp His Asp Glu
             340                345                350
Tyr His Asp His Ala Ile Phe Leu Thr Arg Gln Asp Phe Gly Pro Ser
         355                360                365
Gly Met Gln Gly Tyr Ala Pro Val Thr Gly Met Cys His Pro Val Arg
     370                375                380
Ser Cys Thr Leu Asn His Glu Asp Gly Phe Ser Ser Ala Phe Val Val
385                390                395                400
Ala His Glu Thr Gly His Val Leu Gly Met Glu His Asp Gly Gln Gly
             405                410                415
Asn Arg Cys Gly Asp Glu Val Arg Leu Gly Ser Ile Met Ala Pro Leu
             420                425                430
```

```
Val Gln Ala Ala Phe His Arg Phe His Trp Ser Arg Cys Ser Gln Gln
        435                 440                 445

Glu Leu Ser Arg Tyr Leu His Ser Tyr Asp Cys Leu Arg Asp Asp Pro
    450                 455                 460

Phe Thr His Asp Trp Pro Ala Leu Pro Gln Leu Pro Gly Leu His Tyr
465                 470                 475                 480

Ser Met Asn Glu Gln Cys Arg Phe Asp Phe Gly Leu Gly Tyr Met Met
                485                 490                 495

Cys Thr Ala Phe Arg Thr Phe Asp Pro Cys Lys Gln Leu Trp Cys Ser
            500                 505                 510

His Pro Asp Asn Pro Tyr Phe Cys Lys Thr Lys Lys Gly Pro Pro Leu
        515                 520                 525

Asp Gly Thr Met Cys Ala Pro Gly Lys His Cys Phe Lys Gly His Cys
    530                 535                 540

Ile Trp Leu Thr Pro Asp Ile Leu Lys Arg Asp Gly Asn Trp Gly Ala
545                 550                 555                 560

Trp Ser Pro Phe Gly Ser Cys Ser Arg Thr Cys Gly Thr Gly Val Lys
                565                 570                 575

Phe Arg Thr Arg Gln Cys Asp Asn Pro His Pro Ala Asn Gly Gly Arg
            580                 585                 590

Thr Cys Ser Gly Leu Ala Tyr Asp Phe Gln Leu Cys Asn Ser Gln Asp
        595                 600                 605

Cys Pro Asp Ala Leu Ala Asp Phe Arg Glu Glu Gln Cys Arg Gln Trp
    610                 615                 620

Asp Leu Tyr Phe Glu His Gly Asp Ala Gln His His Trp Leu Pro His
625                 630                 635                 640

Glu His Arg Asp Ala Lys Glu Arg Cys His Leu Tyr Cys Glu Ser Lys
                645                 650                 655

Glu Thr Gly Glu Val Val Ser Met Lys Arg Met Val His Asp Gly Thr
            660                 665                 670

Arg Cys Ser Tyr Lys Asp Ala Phe Ser Leu Cys Val Arg Gly Asp Cys
        675                 680                 685

Arg Lys Val Gly Cys Asp Gly Val Ile Gly Ser Ser Lys Gln Glu Asp
    690                 695                 700

Lys Cys Gly Val Cys Gly Gly Asp Asn Ser His Cys Lys Val Val Lys
705                 710                 715                 720

Gly Thr Phe Ser Arg Ser Pro Lys Lys Leu Gly Tyr Ile Lys Met Phe
                725                 730                 735

Glu Ile Pro Ala Gly Ala Arg His Leu Leu Ile Gln Glu Ala Asp Thr
            740                 745                 750

Thr Ser His His Leu Ala Val Lys Asn Leu Glu Thr Gly Lys Phe Ile
        755                 760                 765

Leu Asn Glu Glu Asn Asp Val Asp Pro Asn Ser Lys Thr Phe Ile Ala
    770                 775                 780

Met Gly Val Glu Trp Glu Tyr Arg Asp Glu Asp Gly Arg Glu Thr Leu
785                 790                 795                 800

Gln Thr Met Gly Pro Leu His Gly Thr Ile Thr Val Leu Val Ile Pro
                805                 810                 815

Glu Gly Asp Ala Arg Ile Ser Leu Thr Tyr Lys Tyr Met Ile His Glu
            820                 825                 830

Asp Ser Leu Asn Val Asp Asn Asn Val Leu Glu Asp Asp Ser Val
        835                 840                 845
```

-continued

```
Gly Tyr Glu Trp Ala Leu Lys Lys Trp Ser Pro Cys Ser Lys Pro Cys
    850                 855                 860

Gly Gly Gly Ser Gln Phe Thr Lys Tyr Gly Cys Arg Arg Arg Leu Asp
865                 870                 875                 880

His Lys Met Val His Arg Gly Phe Cys Asp Ser Val Ser Lys Pro Lys
                885                 890                 895

Ala Ile Arg Arg Thr Cys Asn Pro Gln Glu Cys Ser Gln Pro Val Trp
            900                 905                 910

Val Thr Gly Glu Trp Glu Pro Cys Ser Arg Ser Cys Gly Arg Thr Gly
        915                 920                 925

Met Gln Val Arg Ser Val Arg Cys Val Gln Pro Leu His Asn Asn Thr
    930                 935                 940

Thr Arg Ser Val His Thr Lys His Cys Asn Asp Ala Arg Pro Glu Gly
945                 950                 955                 960

Arg Arg Ala Cys Asn Arg Glu Leu Cys
                965
```

AGENT AND METHOD FOR MODULATION OF CELL MIGRATION

CROSS-REFERENCE TO RELATED APPLICATIONS

This application claims the benefit of provisional patent applications No. 60/087,170, filed May 29, 1998, and 60/129,023, filed Apr. 13, 1999, each of which is incorporated herein by reference in its entirety.

STATEMENT REGARDING FEDERALLY SPONSORED RESEARCH OR DEVELOPMENT

To be determined.

BACKGROUND OF THE INVENTION

Cell migration, particularly migration of cancerous cells and nerve cells, is not well understood, nor are the factors that affect cell migration and tissue shaping in vivo. There is a need in the art to identify and exploit such factors, including but not limited to those involved in normal or abnormal organogenesis. The art also lacks efficient systems for evaluating therapeutic modulators of such functions in vivo and lacks diagnostic methods for assessing the ability of a cell or cell mass to migrate in vivo.

Organogenesis processes in vertebrates proceed in a manner similar to those observed in the common laboratory nematode *C. elegans*. As such, the generation of *C. elegans* gonadal structures can serve as a simple system for investigating developmental morphogenetic processes shared by higher and lower organisms.

In one common morphogenetic process, a tissue bud extends to form an elongate tube with a proximal to distal axis. An emerging theme in bud extension is the presence of specialized regulatory cells at the bud tip that govern elongation. In vertebrate development, this process is seen in extension of the limb (Johnson and Tabin, 1997; Martin, 1998), ureter (Vainio and Muller, 1997), and lung branches (Hogan, 1998). In the *C. elegans* gonad, long "arms" develop by elongation of buds originating from a gonadal primordium. Each gonadal arm possesses a single "leader cell" that serves this regulatory role (Kimble and White, 1981). The biology of distal tip cell migration during gonadogenesis is known to one skilled in the art of *C. elegans* developmental biology. Indeed, the *C. elegans* gonadal leader cells are among the best defined cells that regulate bud elongation, and therefore serve as a paradigm for investigating this common morphogenetic process.

A second common morphogenetic process of organogenesis is the formation of a complex, differentiated epithelial tube. Formation of a complex epithelial tube can involve an initial condensation of mesenchymal cells, followed by epithelialization, lumen formation, and differentiation into modular units. Vertebrate examples include the kidney tubules (Vainio and Muller, 1997) and heart tube (Fishman and Olson, 1997). Similarly, during *C. elegans* gonadogenesis, cells coalesce to form a compact larval structure called the somatic gonadal primordium (SGP). Following formation of this primordium, cell division and differentiation are accompanied by epithelialization and lumen formation to form a complex tube composed of distinct modular units: the uterus, spermathecae and sheaths in hermaphrodites, and the seminal vesicle and vas deferens in males (Kimble and Hirsh, 1979).

Previous studies have identified several genes in *C. elegans* that influence gonadal morphogenesis. One group of such genes includes unc-5, unc-6, and unc-40, which control the direction of leader cell migration (Hedgecock et al, 1990). Normally, leader cells migrate in one direction, then move dorsally, and finally move in the opposite direction to generate a reflexed gonadal arm. In the absence of unc-5, unc-6, or unc-40, the leader cells fail to turn dorsally. Another gene, ced-5, causes the leader cell to makes extra turns or stop prematurely (Wu and Horvitz, 1998). Therefore, in these mutants, the leader cells migrate, but do not navigate correctly, which results in a failure of the gonadal arms to acquire their normal U-shape. In addition to these genes, others are required for specification of cell fates and also influence morphogenesis (lin-12: Greenwald et al., 1983, Newman et al., 1995; lin-17: Sternberg and Horvitz, 1988; lag-2: Lambie and Kimble, 1991; ceh-18: Greenstein et al., 1994, Rose et al., 1997; lin-26: den Boer et al., 1998).

A known *C. elegans* genetic locus, gon-1, defined by one or more mutants, is essential for extension of gonadal germline arms, but is not responsible for signaling the germline to proliferate. In *C. elegans* hermaphrodites, GON-1 is required for migration of two distal tip cells to produce two elongated tubes, whereas in males, gon-1 activity is required for migration of a single linker cell to produce a single elongated tube. In gon-1 mutant hermaphrodites, the leader cells are born normally in the somatic gonadal cell lineage and function normally to promote germline proliferation, but they fail to migrate and do not support arm extension. Similarly in males, the leader cell does not move and no arm extension occurs. The gon-1 locus has not heretofore been mapped with particularity to a nucleic acid coding sequence.

Clarification of the genetic basis for *C. elegans* gon-1 activity would permit one to apply molecular tools to the study of cell migration in a convenient system. It would be particularly advantageous to find that the gon-1 locus encodes a protein having structural relationship to proteins of species that are not readily studied in the laboratory, since one would be able to evaluate those proteins in the convenient *C. elegans* system. Such a system would also provide a means for evaluating agents that can modulate the activity of such genes and proteins and would both facilitate understanding the factors involved in cell migration.

BRIEF SUMMARY OF THE INVENTION

In one aspect, the invention can be an isolated polynucleotide coding sequence that encodes a protein the includes both a metalloprotease domain and at least one thrombospodin type 1 domain, where the protein can direct either cell migration or tissue shaping in an analytical system in a target organism as disclosed herein. In another aspect, the invention can also be a variant of the isolated polynucleotide coding sequence that encodes a protein that shares at least 20%, more preferably 50%, still more preferably 70% and most preferably 80% amino acid sequence identity (using GCG Pileup program) with any of the foregoing in the metalloprotease and thrombospondin type 1 domains while also comprising the amino acids of those domains known to those skilled in the art to be required for protein activity. A suitable variant polynucleotide can hybridize under stringent hybridization conditions known to those skilled in the art to a polynucleotide sequence that encodes a protein that can direct cell migration or tissue shaping in the target organism. In one embodiment, a variant polynucleotide can hybridize under stringent hybridization conditions to a *C. elegans* gon-1 coding sequence. The variant polynucleotide sequence can be a polynucleotide obtained from an organism or can be a mutated version of any polynucleotide sequence noted above. The variant polynucleotide can encode a protein that is identical or altered relative to the wild-type *C. elegans* GON-1 protein. The encoded protein can have enhanced or reduced activity in vivo relative to GON-1.

In a related aspect, a polynucleotide coding sequence that encodes a protein having structural and functional similarity with a wild-type or altered migration or shaping protein can also be substituted, in whole or in part, with structurally related or unrelated sequences to encode a heterologous protein or a chimeric protein in the disclosed system, as detailed below.

Applicants herein disclose that the *Caenorhabditis elegans* gon-1 activity is encoded by a polynucleotide coding sequence (gon-1; SEQ ID NO:1) that encodes an essential protein (GON-1; SEQ ID NO:2) that directs migration of a growing gonadal tube through surrounding basement membranes during gonadogenesis in the nematode and also controls gonadal shape and organ localization.

The migration directing ability and tissue shaping ability are separable and depend upon whether the gon-1 coding sequence is expressed in distal tip cells or in muscle cells, respectively. In wild-type *C. elegans*, a gonad of normal shape is produced when gon-1 is expressed in both cell types. Accordingly, one aspect of the invention can also be a method for shaping a tissue by selectively expressing a protein associated with both tissue elongation and tissue expansion. GON-1 shares significant amino acid identity with proteins that have been noted in other species.

In a related aspect, the invention can be an isolated and substantially purified preparation of a GON-1 protein, an altered GON-1 protein, a heterologous protein, a chimeric protein, or a variant thereof (referred to herein as "an MPT protein", for reasons discussed below), which can be a target for in vivo screening of putative therapeutic modulators, or can be assayed in a diagnostic method for assessing the ability of a cell or cell mass to migrate in vivo, or can be exploited as a therapeutic agent to modulate (increase or decrease) in vivo cell migration.

One skilled in the art will appreciate that the nucleotide coding sequences and encoded amino acid sequences that fall within the scope of the invention are also subject to natural variation or intentional manipulation (e.g., changes in the nucleotide or amino acid sequence) in ways that do not affect the ability to function as described herein. One skilled in that art also understands that the applicants cannot provide a complete list of nucleotide coding sequences and amino acid sequences that can function in the methods of the invention. However, in view of the high level of understanding in the art about the amino acids required for activity of proteins that comprise a metalloprotease domain and proteins that comprise a thrombospondin domain, applicants maintain that a skilled artisan can readily determine whether a protein contains both domains. Stöcker, W. et al., "The metzincins—Topological and sequential relations between the atacins, adamalysins, serralysins, and matrixings (collagenases) define a superfamily of zinc-peptidases," *Protein Science* 4:823–840 (1995), Rawlings, N. D. and A. J. Barrett, "Evolutionary families of metallopeptidases, *Methods in Enzymology* 248:183–228 (1995), and Adams, J. C. et al., *The Thrombospondin Gene Family*, R. G. Landes Company, Austin, Tex. (1995), all incorporated herein by reference in their entirety, provide sufficient guidance to permit those in the art to establish whether a protein comprises both a metalloprotease and a thrombospondin domain.

The invention is further summarized in that an antibody can be produced against characteristic epitopes of any of the foregoing proteins using standard methods. The antibody can be used both diagnostically to ascertain the presence of an MPT protein, or therapeutically to interfere with activity of the MPT protein.

The present invention is also summarized in that an animal that contains a gon-1 allele (or homolog or variant thereof) is a convenient screening tool for finding modulators of cell migration. The present invention is thus further summarized in that a method for identifying modulators of the disclosed MPT proteins includes the steps of treating a target organism having a cell that can migrate or be shaped when under control of an MPT protein with at least one potential modulator of migration or shaping and observing in the treated target organism a change in migration or shaping of the cell or tissue attributable to the presence of a modulator. In a preferred embodiment, the cell is a developing gonadal cell in *C. elegans*, although other cells or organs may be similarly regulated by MPT proteins in other organisms.

The ability of the MPT protein to direct a cell or tissue under its influence to migrate or be shaped can be modulated (increased or decreased) in a variety of ways, such as by altering the migration protein's primary, secondary, or tertiary structure, by altering the location or amount of the protein in an organism, by altering the transcriptional or translational regulation of the gene that encodes the protein, or by providing the organism with an agonist or antagonist molecule in an amount sufficient to interact with the MPT protein so as to increase or decrease the ability of the protein to direct migration or shaping.

In a related method, one can also identify nucleic acid sequences required or desired for migration or shaping of such a cell, by treating a target organism with an agent that affects the polynucleotide sequences of the target organism that encode the MPT protein or that participate in regulating expression of the MPT protein, and then identifying sequences affected by the treatment. The sequences identified in the method can be either complete or partial coding sequences or can be regulatory sequences.

It is an object of the present invention to identify a protein and nucleotide sequence encoding same that directs migration or shaping of a cell or tissue.

It is another object of the present invention to provide a method for modulating cell migration or shaping.

It is yet another object of the present invention to provide a system and method for screening putative modulators of migration or shaping of cells or tissues.

It is an advantage of the present invention that agents having a putative effect upon migration or shaping can be screened in a convenient model system rather than in a vertebrate organism.

Other objects, features and advantages of present invention will become apparent upon consideration of the following detailed description taken in conjunction with the accompanying drawings.

BRIEF DESCRIPTION OF THE SEVERAL VIEWS OF THE DRAWINGS

FIG. 1A depicts a schematic map of the gon 1 locus in *C. elegans* from which the gene was cloned and shows the exon-intron structure of gon-1.

FIG. 1B shows a schematic map of *C. elegans* GON1, the location of five protein-truncating stop mutants in GON1 and a comparison to the protein structures of the murine ADAMTS-1 protein, and the bovine procollagen-I N-proteinase (P1NP) protein. From left to right, GON1 includes a prodomain, a metalloprotease domain, a first cysteine rich region, a thronibospondin type I motif, a second cysteine rich region, and a plurality of thrombospondin type I-like motifs. The five mutants are identified as q518 (aa591 TG$\underline{G}$->TG$\underline{A}$), e2551 (aa1069 TG$\underline{G}$->T$\underline{A}$G), e2547 (aa1229 TG$\underline{G}$->TG$\underline{A}$), q18 (aa1234 TG$\underline{G}$->T$\underline{A}$G) W->stop, and e1254 (aa1345 $\underline{C}$GA->$\underline{T}$GA) R->stop).

FIG. 1C compares the *C. elegans* GON1 amino acid sequence (SEQ ID NO:2) to sequences of the ADAMTS-1 (SEQ ID NO:4) and PN1P (SEQ ID NO:5) proteins. In the metalloprotease domain, amino acids important for enzymatic activity are marked by an asterisk (*). Three conserved histidines (GON1, aa 424, 428, 434) bind a catalytically essential $Zn_{+2}$ ion in well characterized metalloproteases, while a glutamic acid residue (GON1, an 425) is thought to be directly involved in cleavage (Stöcker et al, 1995). In addition, two conserved glycines and a downstream methionine seem to be important for structure of the active site. GON1 bears one of the glycines (aa 427) and the methionine (aa 454), but the second glycine is changed to serine in GON1 (aa431). In the canonical TSPt1 domain, amino acids conserved in vertebrate TSP type-1repeats are shown by a plus (+). The mutation, GON1 (q518), is marked by an inverted triangle (V). For the TSPt1-like repeats, only 2 of the 17 are shown. The consensus sequence for these repeats is: $W-X_{4-5}-W-X_2-CS-X_2-CG-X_{4-5}-X-G-X_3-R-X_3-C-X_{4-27}C-X_{8-12}-C-X_{3-4}-C$ (SEQ ID NQ:3). Because only the first two TSPt1-like motifs are shown, the other mutations are not indicated in this figure.

FIG. 2A depicts normal morphogenesis of the *C. elegans* hermaphrodite gonad.

FIG. 2B shows that arm extension does not occur in gon-1 mutants and that the gonad develops as a disorganized mass of somatic and germline tissues. Similarly, in males, the gon-1 mutant gonad is severely disorganized and does not acquire its normal shape.

DETAILED DESCRIPTION OF THE PREFERRED EMBODIMENTS

The existence of a protein in *C. elegans* required for cell migration or shaping has not heretofore been known, nor has any function been previously ascribed to a protein encoded by the designated sequence. The inventors have determined that a functional GON-1 protein is required for migration of the regulatory cells that lead the developing gonad organ during its migration. GON-1 is also involved in shaping tissues such as gonads. By appreciating the role of GON-1 (and the gon-1 gene) and its relationship to a related gene that is upregulated in a metastatic tumor cell, the inventors have identified a gene and protein believed to be fundamental in the process of normal and abnormal cell migration and tissue shaping. The gene and protein, and related genes and proteins, can be utilized in the methods of the invention as described herein. References herein to influencing cell migration are also intended to encompass shaping of tissues or organs. Likewise, references to a migration protein encompass proteins of the same class that can also be used in methods for shaping tissues or organs.

Generally speaking, the methods of the present invention permit one to identify agents that modulate cell migration or tissue shaping in vivo or in vitro. One can treat target organisms with panels of polynucleotides, proteins, sugars, lipids, organic molecules, other chemicals, synthetic or natural pharmaceutical agents or other agents to determine whether any agent affects activity of an MST protein. This list is necessarily incomplete, since one cannot predict in advance which agents will be effective. However, applicants have enabled a system for screening panels of putative agents, in accord with the common practices of pharmaceutical companies that typically screen thousands of compounds against a test system in an effort to reveal preferred agents. Candidate agents likely to modulate MPT proteins in the disclosed system include tissue inhibitors of metalloproteases and pharmaceutical metalloprotease inhibitors or enhancers such as those from British Biotech. Inhibitors or enhancers of thrombospondin activity are also good candidate agents.

Agents so identified can be used therapeutically to enhance or inhibit cell migration or to influence tissue shape. Agents having an adverse or inhibiting or knock-out effect upon activity of a migration protein can also be used in a method for biocontrol of animals that employ the migration protein in gonadal development, where the method includes the step of exposing a developing animal to an amount of the agent effective to prevent gonadal development such that the animals are rendered sterile. While this biocontrol method is particularly envisioned for use in nematodes, it may be applicable to other animals as well, since genes related structurally and functionally to gon-1 are known to exist in animals as diverse as nematodes, cattle and humans.

Using the invention one can also identify polynucleotide sequences including coding and regulatory sequences that affect activity of a migration protein. For example, null or so-called reduced activity mutants can be mutagenized and assayed for activity-restoring, activity-inhibiting or activity-enhancing changes. By extension, one can perform comparable screens ad infinitum on sequences identified in this manner, to obtain still more sequences that have an indirect effect on migration activity. After identifying such sequences in a target organism, one can obtain homologous polynucleotides from other organisms by screening nucleic acid libraries under stringent hybridization conditions in a manner known to those skilled in the art.

A method for evaluating putative modulators of cell migration preferably employs a nematode as a target organism. The methods may be advantageously practiced using a nematode that comprises a migration protein as described herein, or a mutant nematode that either lacks a migration protein or contains a migration protein having reduced activity. The protein can be encoded by wild-type *C. elegans* gon-1 (disclosed herein), by a mutant that confers upon the nematode an enhanced or reduced sensitivity to modulators, by a transgene from another organism, in whole or in part, or by a variant of any of the foregoing. Nematodes are desirable target organisms, in general, because they are easy to grow and maintain, and easy to assay, particularly because they are transparent.

Nematodes are also particularly desired because the powerful techniques of reverse genetics can be employed. One can also target specific *C. elegans* sequences for mutation or RNA-mediated interference (a technique used to transiently knock genes out by RNA injection) to identify nucleic acid and protein sequences that have a direct inhibitory or enhancing effect on gon-1 activity.

With the identification of the gon-1 gene and GON-1 protein in *C. elegans* and the discovery of homologous genes in other species, the functions of migration proteins can be analyzed in vivo during organogenesis using the full force of molecular genetics available in that system. Such functions can include, but may not be limited to cell migration, basement membrane remodeling, and tubular organ formation.

Although the system is exemplified in *C. elegans*, a free-living (i.e., non-parasitic) nematode, those skilled in the art can develop similar systems operating on the same principles without undue experimentation in other convenient organisms, including other nematodes including, without limitation, *C. briggsae*, or in, for example, Drosophila, or other organisms conveniently studied in the laboratory. To do so, one would only need to identify the homolog of gon-1 in such an organism, using standard molecular biological methods and then screen for related genes, proteins and other factors as described herein. One could also use such systems in other animals to study transgenes in ways comparable to those described herein. Those skilled in the art can produce transgenic animals of many species without undue experimentation.

In the method, a putative modulator is provided to the target organism, for example, by adding it to the growth media, by injecting it into the organism or by gene transformation technology. The effects of said modulator can be assessed either by screening for changes in cell migration or by genetic selection for fertile animals. The assessment methods are known to those skilled in the art. *Caenorhabditis elegans*: Modern Biological Analysis of an Organism, Methods in Cell Biology, volume 48, Epstein, H. F. and D.C. Shakes, eds., Academic Press (1995), incorporated herein by reference in its entirety, describes suitable methods and conditions for growing and monitoring *C. elegans*.

Figure 1C:
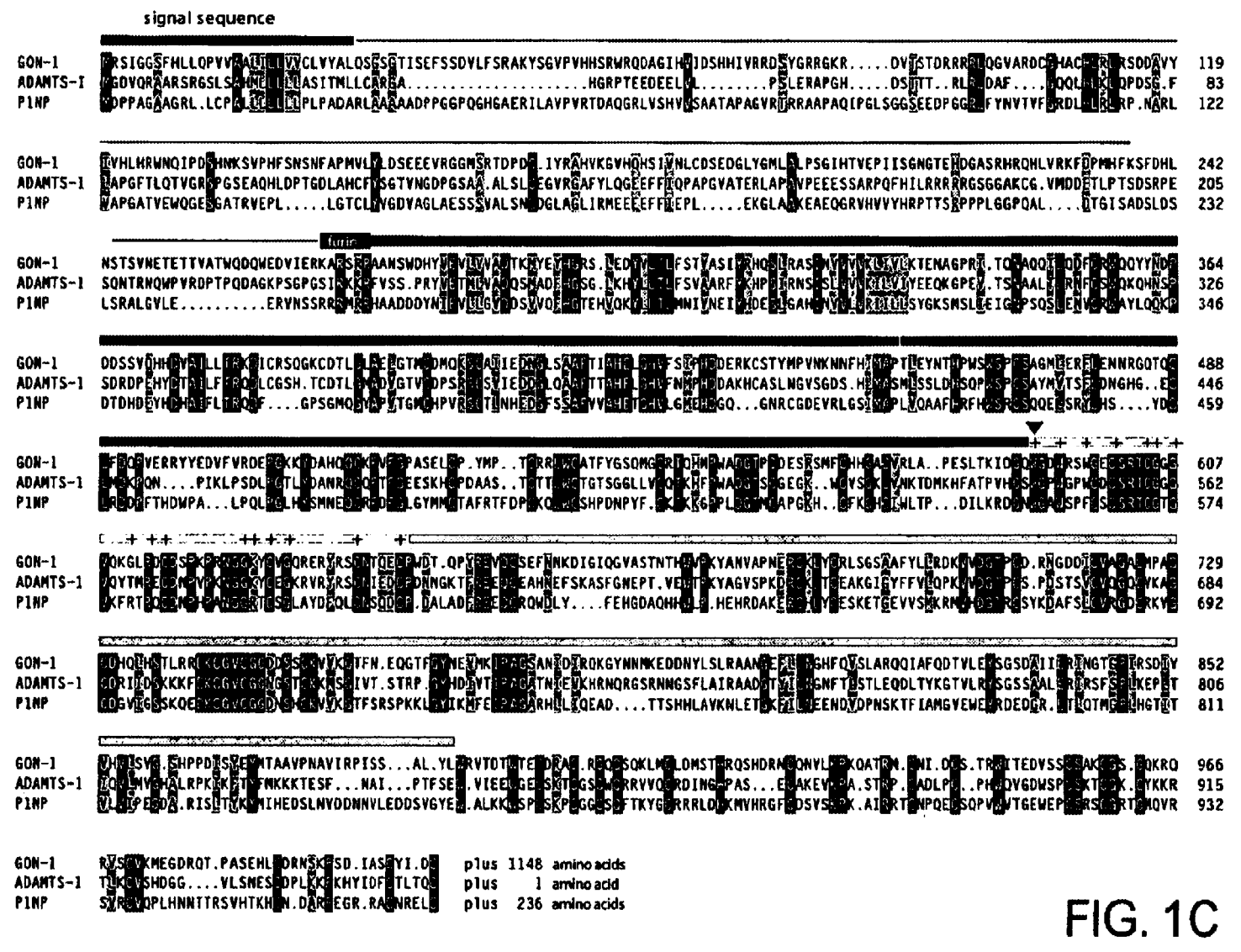

*C. elegans* GON-1 is characterized by a multi-domain structure that includes several known motifs. GON-1 protein is a secreted metalloproteinase that lacks a transmembrane domain and possesses a predicted metalloprotease domain between amino acids 269–456. The metalloprotease enzymatic activity is essential for GON-1 function; proteins that might be cleaved by this metalloproteinase include components of the basement membrane and other proteins that modulate migration. The metalloprotease domain shares sequence similarity with other metalloproteinase enzymes. In addition to its metalloprotease domain, GON-1 possesses a series of consecutive motifs that are related to, but variants of, the thrombospondin type 1 (TSPt1) repeats (FIGS. 1B, C). The most N-terminal TSPt1 repeat bears the hallmarks of this type of motif in vertebrate thrombospondins (15/16 of the consensus amino acids, + in FIG. 1C) (Adams et al., 1995), whereas the remaining 17 repeats are less similar and define a TSPt1-like variant. Proteins that might interact with this domain include proteins that modulate migration, including but not limited to components of the basement membrane.

GON-1 is similar to members of the reprolysin subfamily (Rawlings, N. D. and A. J. Barrett, "Evolutionary families of metallopeptidases, *Methods in Enzymology* 248:183–228 (1995), incorporated herein by reference in its entirety). At the N-terminal border of the metalloprotease domain, there is a potential furin cleavage site (FIG. 1C) (Pei and Weiss, 1995; Pei and Weiss, 1996). GON-1 and the reprolysins share a common zinc binding active site with the larger metzincin superfamily (Stöcker et al., 1995). Amino acid conservation within the active site together with the known crystal structure of several superfamily members reveals those amino acids essential for enzymatic activity (marked by asterisks in FIG. 1c) (ibid). GON-1 has all amino acids implicated in catalysis and all but one implicated in structure of the active site.

Wild-type *C. elegans* GON-1 (SEQ ID NO:2) is suitable for use in the methods of the present invention, although a skilled artisan can replace the *C. elegans* gon-1 coding sequence with a sequence that encodes all or part of a homologous protein, using the standard tools available to a molecular biologist. This mixing and matching can increase or decrease the activity of the encoded chimeric protein. As described elsewhere herein, it can be desirable to provide a system having reduced or enhanced migration activity, or even no migration activity, depending upon whether one is evaluating agents that enhance or inhibit migration. Increased gene activity is characterized either by increased gonadal arm extension, increased compactness of gonadal tissue, or fertility. Decreased gene activity is assayed either by decreased gonadal arm extension, decreased compactness of gonadal tissue or sterility. Certain specific activity-reducing mutations in gon-1 are described in the Examples.

Sequences with related structures have already been isolated from vertebrate organisms, but no related invertebrate sequence is known to the inventors. Still other related metalloprotease proteins (and polynucleotide sequences encoding same) will be isolated from vertebrate and invertebrate organisms. While the *C. elegans* gon-1 protein includes 17 thrombospondin domains, the bovine and murine homologs include only 2 such domains. Other known members of the family also have one canonical TSPt1 repeat, can contain at least one TSPt1-like variant repeat, and contain two conserved cysteine rich regions. Based on this conserved architecture, we suggest the name MPT (for MetalloProtease with TSP1 repeats) for the family.

While the in vivo functions of these proteins may differ from that of *C. elegans* GON-1, these proteins are expected to function in place of GON-1 in whole or in part in the disclosed methods. All such homologs from other vertebrate and invertebrate organisms (and the polynucleotide sequences that encode such homologs), variants thereof, and chimerics that incorporate portions thereof, whether obtained naturally or induced in the laboratory using the tools available to a molecular biologist, are considered to be useful in the present invention. In particular, functional domains, such as the metalloprotease domain, can be swapped into corresponding domains in gon-1.

The amino acid sequences of GON-1, ADAMTS-1 and bovine PN1P are compared in Fig. 1C. The additional thrombospondin domains of GON-1 not found in ADAMTS-1 or PN1P are not shown in FIG. 1C. Those portions of GON-1 that have no obvious relationship to known motifs are conserved among the family of GON-1 homologs. The GON-1 protein shows significant sequence similarity to the bovine procollagen-1 N-proteinase (P1NP), to the murine ADAMTS-1 protein, and to a pair of human aggrecan-degrading metalloprotease-encoding sequences described in International Patent Application Number PCT/US98/15438, published on Feb. 4, 1999 as International Publication No. WO 99/05291, incorporated herein by reference in its entirety. Another human homolog which has significant identity to the bovine PLNP has Genbank accession number d1021662.

Bovine P1NP can proteolyze the N-terminal propeptide from collagen I (Colige et al., 1995, Colige et al., 1997). Metalloprotease activity is required for GON-1 function and suggest that, like P1NP, it may cleave components of the extracellular matrix. Murine adamts-1 expression correlates with tumor cell progression (Kuno et al., 1997). The murine ADAMTS-1 protein is found in an advanced cachexogenic murine tumor cell. Human aggrecanase has been associated with arthritis in humans. Given the role of GON-1 in regulating cell migration of the *C. elegans* leader cell, we suggest that MPT proteins may be involved more generally in cell migrations that must pass through extracellular matrix and that, in cancerous tissues, loss of MPT regulation may promote metastasis. The percent identity of the identified domains of *C. elegans* GON-1 with the bovine and murine proteins is shown in FIG. 1B.

Changes can be made in any of the foregoing at the nucleic acid level in a manner known to those skilled in the art, by, for example, removing a section of the coding sequence, interrupting the coding sequence with an additional sequence, rearranging at least one section of the gene, or by providing in the sequence other changes that can include but are not limited to point mutations that either truncate the protein or disable an active site in the protein encoded by the altered polynucleotide.

Changes can also be made by altering the transcription or translation of the gene that encodes the migration protein by altering in a manner known to the art the upstream and/or downstream regulatory sequences that the surround the gene. Likewise the translation-regulating elements of an mRNA encoding the migration protein can also be altered to affect the stability or location of the mRNA. An antisense RNA can also interfere with translation of the migration protein.

At the protein level, one skilled in the art can modulate the activity of the migration protein either by modifying the protein encoded by the gene as noted above or by directing the protein to be modified in vivo, for example, by providing in the protein appropriate signal or signals for cleavage or degradation by other cellular factors. Alternatively, the protein can be targeted with an activity-modulating factor such as a protein, a peptide, or an organic or inorganic co-factor. Any of these factors can, for example, occupy or obstruct an active site of the protein which is required for activity. Likewise, if the activity of the protein is natively regulated by an endogenous co-factor, an effect can be achieved by modulating the availability of the native co-factor.

One skilled in art is familiar with the techniques associated with the aforementioned alterations, including the production of any construct necessary to effect such changes. One skilled in the art also understands that changes in the primary amino acid sequence (including, e.g., substitutions, deletions, additions, inversions) may or may not alter the activity of a protein, depending upon the position and the extent of the change.

For purposes of this application a migration protein is considered active if it causes a cell that comprises the protein, or a cell that is under the influence of the protein, to migrate to any appreciable extent. A cell is "under the influence of the protein" if the cell migrates in the presence of the protein, even if the cell does not contain the protein. In vivo, the cell from which the protein is secreted and its site of action remain unknown.

Non-native transgene sequences containing non-native sequences homologous to all or part of *C. elegans* gon-1 can be introduced into *C. elegans* on an expressible genetic construct that contains a promoter that drives expression in a tissue that allows easy assay so that the effect or effects of those sequences on migration and other functions can be evaluated in the system. Methods for generating and selecting transgenic nematodes are well-known in the art. Transgenic animals can rescue null mutants or can suppress or enhance the activity in the reduced-activity mutants. A preferred example of a transgene sequence is a human gon-1 homolog sequence, although any of homolog can be used. Some constructs may contain all or part of the gon-1 coding sequences. The transgene should be appropriately expressed near the cells to be controlled by the migration protein. In *C. elegans*, the gon-1 promoter, active in leader cells and in muscle cells, is suitable. Other promoters that can be used in *C. elegans* include the lag-2 promoter, which drives expression in the hermaphrodite distal tip cells, and the unc-54 promoter which drives expression in body wall muscle.

One can assay for effects of treatment with a potential modulating agent on cell migration and gonadal tube extension by comparing migration after treatment to the cell migration in either a wild-type organism or to that in an untreated, previously characterized mutant. Before treatment in the methods, if the migration protein is expressed in leader cells at wild-type levels, directed elongation of gonadal arms along a proximal-distal axis is observed. If the migration protein is expressed in muscle, on the other hand, one observes more dispersed activity, which may be important for expansion as the gonad along the dorsal-ventral and left-right axes. If a migration protein having a level of activity comparable to that of the wild type protein is expressed from a polynucleotide sequence under control of the native gon-1 promoter, of course, normal gonadal development is observed, as is shown in FIG. 2A. FIG. 2B shows that arm extension does not occur in gon-1 mutants and that the gonad develops as a disorganized mass of somatic and germline tissues. Similarly, in males, the gon-1 mutant gonad is severely disorganized and does not acquire its normal shape. Both wild-type activity and the mutant phenotype can be modified by treatment according to the methods. One can also direct the shape of a tissue or organ by introducing a transgene coding sequence under control of a promoter selected to express the transgene coding sequence in a desired tissue or cell type.

One can also assess whether a cell has the potential for migration by analyzing for example, the level of the migration protein in the cell, or the level at which the RNA encoding the migration protein is present. A diagnostic assay for the presence of active site residues in the protein can also be devised. Likewise, the presence or absence of a DNA sequence encoding an essential aspect of the protein can also be used in a diagnostic manner to assess the likelihood of cell migration.

Our finding that GON-1 is tightly regulated to achieve arm extension during gonadogenesis in *C. elegans* suggests that similar activities may play similar roles in the morphogenesis of organs throughout the animal kingdom. Previous in vitro experiments support this notion. For example, antibodies recognizing matrix metalloprotease 9 (MM9) can block branching of the ureter bud during kidney development (Lelongt et al., 1997), and inhibitors of MMPs block the invasion of endothelium cells into a fibrin matrix in assays for angiogenesis (Hiraoka et al., 1998). Based on these observations and our analysis of GON-1, we suggest that the MPT metalloproteases are critical modulators of organogenesis.

Whether the target organism contains a wild-type *C. elegans* gon-1 gene, a mutant gon-1 gene or a transgene substituted in place of gon-1, in whole or in part, the system is readily used to identify other genes, proteins, drugs, chemicals or other factors that either enhance or antagonize activity.

In a method for increasing the migration of the cell, the native protein or related protein or a genetic construct encoding same can be administered to, or caused to be expressed at a high level in, the target cell. Alternatively, an enhancing factor can be provided inside or outside the target cell, as appropriate. Where it is desired to decrease migration of a targeted cell, as in the case of a tumor cell, an inhibiting factor can be added into, or the vicinity of, the targeted cell.

The vicinity of the cell is defined as sufficiently close to the targeted cell so as to effect a desired change in the cell migration. If the migration protein is secreted from the cell in which it is produced, the activity of the protein can further be modulated either by preventing secretion of the protein or by interfering with the protein activity outside the cell. If the protein acts outside the target cell, the protein, an active portion thereof, or a modulating factor can be administered to the vicinity in an amount effective to modulate cell migration.

The reproductive sterility that can result from inhibited migration of developing gonadal cells under the control of an migration protein that is inactive or has reduced activity can be further exploited, for example, in a method for controlling reproduction of an organism that relies upon a migration protein during gonadogenesis. An organism for which such control would be appropriate would include *C. elegans* and other nematodes or parasites, and could include other invertebrates, as well as vertebrate species including, for example, avian, amphibian, reptilian and mammalian species.

With an appreciation for the migration proteins of the invention, normal and abnormal cell migration attributable to activity of a migration protein can be therapeutically increased or decreased. The mechanisms by which the gene and protein are regulated can be determined by one skilled in the art and can be advantageously exploited to modulate expression of the migration protein at either the nucleic acid or protein levels.

EXAMPLES

To gain molecular insight into gon-1 function, we cloned the gene by a combination of fine genetic mapping, mutant rescue and RNA-mediated interference. Mutations in the gon-1 gene were finely mapped by genetic crosses with respect to markers that had already been placed on the physical map. Cosmids in the region were next tested for mutant rescue of the gon-1 mutations. The genomic *C. elegans* sequence that includes the coding sequence of the gon-1 gene in a plurality of exons is found on cosmids F25H8 (Accession # 69360) and T13H10 (Accession #69361); T13H10 bears most of gon-1 and rescued the gon-1 phenotype. The predicted open reading frames on this cosmid were tested by RNA-mediated interference to identify the transcript corresponding to gon-1 activity. The identification of this transcript as gon-1 was then confirmed by subcloning and mutant rescue by a smaller region of the cosmid that contained that transcript, by RNA-mediated interference, and by identifying gon-1 mutations in the coding region of this transcript. The positions in the migration protein that correspond to the identified mutations are indicated in FIG. 1B. We confirmed identification of F25H8.3 as gon-1 by identifying molecular lesions for a plurality of gon-1 alleles.

Mutants were obtained as described (Brenner, S. "The Genetics of *Caenohrabditis elegans, Genetics* 77:71–94 (1974), incorporated herein by reference. Each contained an allele of gon-1 that maps to chromosome IV between unc-24 and dpy-20, all are recessive, and all are fully penetrant for sterility. Five alleles, e1254, e2547, q18, q517, and q518, fail to complement the sixth allele, e2551, and, therefore, the mutations define a single gene. Three-factor mapping places gon-1(e2551) 0.08 map units to the right of elt-1 and 0.12 map units to the left of unc-43 at position 4.44. Specifically, among Unc-43 non-Elt-1 recombinants isolated from gon-1/elt-1 unc-43 mothers, 8/13 carried the gon-1 mutation.

To compare allelic strengths, we examined the penetrance of arm extension defects in homozygotes for each allele. In gon-1(q518) homozygotes, no arm extension was observed at 15°, 20° or 25° C. However, in homozygotes for the other gon-1 alleles, some arms extended at least partially. By this measure, the gon-1 alleles can be placed in an allelic series: q518<e2547≅q18<e1254≅q517<e2551. Interestingly, the weaker gon-1 alleles have a more severe defect at lower temperature, which may reflect a cold sensitivity of GON-1 function, or of the process of arm extension itself.

The strongest loss-of-function allele is gon 1(q518) which is a nonsense mutation that resides in the canonical TSP1 motif; the other mutations are located in the TSP1t1-like repeats. gon-1(q518), the nonsense mutant located closest to the N-terminus, has the most severe effect on cell migration; nonsense mutants located closer to the C-terminus than q518 are partially defective for migration. Because the mutant phenotype for gon-1(q518) homozygotes is identical to that of gon-1(q518) hemizygotes and because gon-1(q518) bears a nonsense mutation predicted to remove the bulk of the GON-1 protein, this allele is likely to be a molecular null. Therefore, gon-1(q518) was used for analyzing the roles of gon-1 in gonadal morphogenesis and is referred to as gon-1(0).

Normally, the gonad is a tubular structure with specialized regions. By contrast, in gon-1 mutants, the adult gonadal tissues exist as a disorganized mass with little or no tubular morphology. Specifically, neither arms nor somatic gonadal structures (e.g. uterus, spermatheca) are observed. In all cases, however, the gonads are rendered infertile by these mutations.

In *C. elegans*, mRNAs containing premature stop codons are normally degraded by the smg system, but those mRNAs are stabilized in a smg mutant background (Anderson and Kimble, 1997). Therefore, the remaining activity of truncated GON-1 proteins should be evident in smg-1; gon-1 double mutants. We found that gon-1(q518) was not suppressed in a smg background, whereas all four mutations in the TSP1-like repeats were suppressed. Therefore, while the GON-1(q518) mutant protein that possesses the metalloprotease domain but lacks the bona fide TSPt1 motif (as well as the rest of the protein C-terminally), is not capable of mutant rescue, the other truncated proteins are. The conclusion that two TSPt1-like repeats are sufficient for rescuing activity was confirmed by mutant rescue with a mini-transgene.

The lack of gonadal arms in gon-1 (0) mutants suggested that the leader cells, which normally govern arm extension, may be defective. To assess whether leader cells were generated during development, we first examined the gonadal cell lineages in gon-1(0) mutants during the first two larval stages. Normally, the somatic gonadal progenitor cells, Z1 and Z4, give rise to two leader cells, Z1.aa and Z4.pp, in hermaphrodites, and one leader cell, Z1.pa or Z4.aa, in males (Kimble and Hirsh, 1979). In hermaphrodites, these leader cells are called distal tip cells (DTC), and in males, they are called linker cells (LC). The hermaphrodite distal tip cell is both a leader cell and a regulator of germline proliferation. Kimble, J. E. and J. G. White, "On the control of germ cell development in *Caenorhabditis elegans, Devel. Biol.* 81:208–219 (1981), incorporated herein by reference in its entirety, provides guidance for a skilled artisan on the biology of distal tip cell migration. The information disclosed in that paper can be employed in determining whether an agent modulates cell migration or tissue shaping in a method of the invention.

In gon-1(0) hermaphrodites and males, we found that the timing and pattern of cell divisions of Z1 and Z4 and their descendants were the same as in wild-type during L1 and L2 (data not shown). In particular, Z1.aa and Z1.pp in hermaphrodites and Z1.pa/Z4.aa in males were born at the correct time and place. To ask whether the presumptive hermaphrodite leader cells, Z1.aa and Z4.pp, had adopted the leader fate, we examined expression of a molecular marker for that fate. The unc-5 gene encodes a netrin receptor and is essential for dorsal migration of leader cells (Leung-Hagesteijn et al, 1992). Using a reporter transgene, unc-5::lacZ (J. Culotti, personal communication), we found that unc-5 expression was the same in wild-type and gon-1(0) animals: unc-5 was not expressed during early larval stages, but was activated in late L3 when the DTCs normally turn dorsally during wild-type gonadogenesis.

Since the hermaphrodite leader cells, Z1.aa and Z4.pp, also control germline proliferation, we next asked if they were correctly specified for that regulatory function. To this end, we examined expression of the lag-2 gene, which encodes the DTC signal for germline proliferation (Henderson et al., 1994). Using a reporter transgene, lag-2::GFP, we found that lag-2::GFP expression was similar in wild-type and gon-1 gonads. Furthermore, we ablated Z1.aa and Z4.pp in gon-1(0) mutants and found that germline proliferation was arrested. Therefore, the hermaphrodite DTCs, Z1.aa and Z4.pp, appear to be specified correctly both as leader cells and as regulators of germline proliferation.

Since the leader cells appeared to be specified correctly in gon-1 mutants, we next examined their ability to migrate and lead arm extension. Normally, the hermaphrodite leader cells (distal tip cells) migrate away from the center of the gonad along the anterior-posterior axis, then reflex dorsally, and migrate back. To compare leader cell migration in wild-type and gon-1(0) mutants, we followed their movements throughout gonadal development and at the same time measured gonadal lengths. At the mid-L1 stage, just prior to division of the leader cell progenitors, Z1 and Z4, the length of the gonad from anterior to posterior end was 19 $\mu$m in both wild-type and gon-1(0) mutants. Following division of Z1 and Z4 in late L1, a small difference in gonadal length was discerned: 25 $\mu$m in wild-type vs. 22 $\mu$m in gon-1 mutants. However, in older larvae with differentiated leader cells, the length differences were dramatic. In gon-1(0) hermaphrodites, the distal tip cells had moved little from their birth position and little to no gonad extension had occurred.

A similar defect is observed in males. Normally, the male leader cell (linker cell) migrates anteriorly, then reflexes and migrates to posterior end of the worm. However in gon-1(0) males, the linker cell failed to migrate, and little to no extension had occurred. We conclude that gon-1 is required for leader cell migration and hence gonadal arm extension.

As we observed leader cells during gonadogenesis, we noticed that they assumed an unusual morphology. To explore this further, we examined hermaphrodite DTCs using fluorescence and thin section electron microscopy (EM). Using lag-2::GFP, which is expressed in hermaphrodite DTCs and reveals the extent of their cytoplasm (D. Gao and J. Kimble, unpublished), we found that the wild-type and gon-1(0) DTCs had dramatically different morphologies. In wild-type, the DTC was crescent-shaped with processes extending around the germ line, while in gon-1 mutants, it was round and enlarged. Furthermore, the position of the nucleus within the DTC was variable in gon-1 mutants, whereas in wild-type, it was located at the leading edge of the migrating cell. By EM, we confirmed the difference in morphology between wild-type and gon-1 leader cells and also discovered a difference in subcellular organization. Whereas wild-type leader cells extend processes along the germline, gon-1(0) leader cells do not possess such processes. Furthermore, the plasma membrane is abnormally invaginated in gon-1(0) L3 leader cells, and these membranes accumulate within the cytoplasm of older gon-1(0) mutants.

The lack of gonadal arms is not the only defect in gon-1 mutants. In addition, no gonadal structures (e.g. uterus in hermaphrodites, vas deferens in males) can be discerned. One problem might have been a failure to differentiate gonadal tissues. However, we were able to identify the major somatic gonadal cell types in late L4 gon-1(0) mutants. To see somatic gonadal sheath cells, we used lim-7::GFP, which expresses Green Fluorescent Protein (GFP) in hermaphrodite sheath cells (O. Hobert, pers. comm.). In wild-type, fluorescence from lim-7::GFP encircled the germ cells, while in gon-1 mutants, only irregularly-shaped patches were observed. Similarly, MH27 antibody, which stains spermathecal cells intensely (den Boer et al., 1998), was present in disorganized patches in gon-1 mutants. Finally, cells with a typically uterine morphology were present, but no normal uterine structure was found in gon-1 mutants. Therefore, the gonadal tissues in gon-1(0) mutants appear to differentiate correctly.

One simple explanation for the gross morphogenetic defects of mature gon-1 gonads might have been that all aspects of gonadal morphogenesis are disrupted as a consequence of the defect in leader cell migration. Indeed, by killing the distal tip cells in wild-type animals, we could reproduce the gon-1 mutant phenotype: arms did not extend and gonadal structures were grossly malformed. However, closer inspection suggests that gon-1 has a role in gonad morphogenesis independent of leader cells.

To examine the generation of gonadal somatic structures, we removed the germ line (−GL) from gon-1(0) to permit formation of an essentially normal somatic gonadal primordium at the early L3 stage and we removed both leader cells (−DTCs) and germline (−GL) from wild-type hermaphrodites as a control. The control animals had no arm extension, but formed a normal somatic gonadal primordium. A comparison of gonadal structures at the L4 stage, when they are most easily scored, revealed striking differences. While fragments of uterus were present in gon-1(−GL) hermaphrodites, no coherent uterus was observed. Furthermore, the gon-1 (−GL) gonad was small, and most gonadal had extruded from the gonad proper. By contrast, an apparently normal uterus formed in the wild-type animals lacking both DTCs and germ line. Therefore, gon-1 is required not only for arm extension, but also for morphogenesis of the uterus.

Finally, we asked whether gon-1 functions in the development of non-gonadal tissues. We assayed embryonic viability, the overall shape of the animal, coordination of its movements, mating behavior in males, the male tail, growth rate, and entry and exit into dauer stage of the life cycle: all were normal in gon-1(0) mutants. The normal movement and shape of gon-1(0) mutants suggests that gon-1 is not required generally for cell migration. For example, failure in migration of the CAN neuron causes the tail to wither (Forrester et al., 1998), and defects in axon migration leads to an uncoordinated (Unc) phenotype (Hedgecock et al., 1990). Furthermore, we followed the M sex myoblast and the Q neuroblasts migrations (Antebi et al, 1997)in at least five gon-1(0) mutants, and both were normal. We conclude that gon-1 does not affect cell migrations generally and, furthermore, that gon-1 does not affect the development of non-gonadal cells, tissues or organs. Finally, we examined the non-gonadal tissues in gon-1 mutants that had been operated during L1 to remove Z1–Z4, the four gonadal progenitor cells. This experiment was done, because the disorganized gonadal tissues in gon-1(0) hermaphrodites often cause the animal to explode during adulthood, preventing examination of their non-gonadal tissues at this stage. Although these gonadless gon-1 adults had no gross defects, we observed a reproducible vacuolization in the body wall with differential interference contrast microscopy, which was not seen in similarly treated wild-type animals. However, it must be emphasized that this defect has no apparent developmental consequences. Given the dramatic effects of gon-1 on gonadogenesis, we suggest that the major role of gon-1 in development is to control the shape of the gonad.

The wild-type *C. elegans* gon-1 sequence is shown in SEQ. ID. NO. 1. The protein encoded by SEQ. ID. NO. 1 is shown in full in SEQ. ID. NO. 2 and in part in comparative FIG. 1C.

PROPHETIC EXAMPLE

A target organism that contains a migration protein is treated with one or more potential modulators of migration of a developing gonadal cell. The organism is preferably a nematode, and is more preferably *C. elegans*. The potential modulating agent is administered in an amount typical of any additive to a culture, preferably at a level of several nanograms to several micrograms per milliliter. The organism can contain a native migration protein or a variant form of a native migration protein, or can express a migration protein from a transgene that can be delivered to the organism in a manner known to those skilled in the art. The protein can also be a chimeric protein expressed from a transgenic polynucleotide that comprises sequences from at least one of the foregoing polynucleotides.

Upon examination, it is observed that one can rescue migration in a target that lacks the migration protein by administering an exogenous polynucleotide that encodes a migration protein. In a target that contains a migration protein, one can also identify administered agents that increase or decrease the migration of a developing gonadal cell. One can also treat the genetic material of the target organism using standard methods and treatments and can then identify genetic changes that increase or decrease migration of developing gonadal cells.

We claim:

1. A method for selecting a modulator of a gonadal cell migration activity in a nematode having a developing gonadal cell, the nematode being selected from the group consisting of C. elegans and C. briggsae, the migration activity being selected from the group consisting of elongation and expansion, wherein the migration activity is regulated by a protein that comprises a metalloprotease domain and a thrombospondin domain, the method comprising the steps of:

treating a nematode, with at least one potential modulator thereby producing a treated nematode; and observing in the treated nematode a change in the migration activity of the cell attributable to the at least one potential modulator, wherein the change is not observed after treatment with the potential modulator of a mutant of the nematode that comprises the cell but does not comprise the protein, wherein the change results in the selection of the modulator, wherein the protein is selected from the group consisting of a protein having an amino acid sequence of SEQ ID NO:2, a protein encoded by a heterologous polynucleotide sequence of SEQ ID NO:1 introduced under transcriptional control of a promoter functional in the nematode, a chimeric protein that retains a metalloprotease domain and at least one thrombospondin domain of SEQ ID NO:2, marine ADAMTS-1 protein, bovine procollagen-1 N-proteinase, and human aggrecan-degrading metalloprotease.

2. A method as claimed in claim 1 wherein before the treating step the migration activity is absent or reduced relative to a wild type nematode.

3. A method as claimed in claim 1 wherein the treating step restores or enhances the migration activity.

4. A method as claimed in claim 1 wherein before the treating step the migration activity is at a level of a wild nematode.

5. A method as claimed in claim 1 wherein the treating step reduces the migration activity.

6. A method as claimed in claim 1 wherein the at least one modulator is selected from the group consisting of a nucleic acid molecule, protein molecule, a sugar, a lipid, an organic molecule, a synthetic or natural pharmaceutical agent, and a mixture thereof.

7. A method as claimed in claim 1 wherein before the treating step the protein is non-functional.

8. A method as claimed in claim 7 wherein the modulator is a nucleic acid molecule that encodes the protein.

9. A method as claimed in claim 7 wherein the modulator is die protein.

* * * * *